United States Patent
Hong et al.

(10) Patent No.: US 12,152,263 B2
(45) Date of Patent: Nov. 26, 2024

(54) TRANSAMINASE MUTANT AND USE THEREOF

(71) Applicant: ASYMCHEM LIFE SCIENCE (TIANJIN) CO., LTD., Tianjin (CN)

(72) Inventors: Hao Hong, Morrisville, NC (US); Gage James, Morrisville, NC (US); Na Zhang, Tianjin (CN); Fang Liu, Tianjin (CN); Junjie Yan, Tianjin (CN); Ye Liu, Tianjin (CN); Zujian Wang, Tianjin (CN)

(73) Assignee: ASYMCHEM LIFE SCIENCE (TIANJIN) CO., LTD., Tianjin (CN)

( * ) Notice: Subject to any disclaimer, the term of this patent is extended or adjusted under 35 U.S.C. 154(b) by 503 days.

(21) Appl. No.: 17/615,262

(22) PCT Filed: May 30, 2019

(86) PCT No.: PCT/CN2019/089170
§ 371 (c)(1),
(2) Date: Nov. 30, 2021

(87) PCT Pub. No.: WO2020/237552
PCT Pub. Date: Dec. 3, 2020

(65) Prior Publication Data
US 2022/0220519 A1   Jul. 14, 2022

(51) Int. Cl.
| C12N 15/70 | (2006.01) |
| C12N 9/10 | (2006.01) |
| C12P 13/00 | (2006.01) |
| C12P 17/12 | (2006.01) |

(52) U.S. Cl.
CPC .......... *C12P 13/001* (2013.01); *C12N 9/1096* (2013.01); *C12P 17/12* (2013.01); *C12Y 206/01* (2013.01)

(58) Field of Classification Search
CPC .......... C12N 15/70; C12N 9/10; C12Y 206/01
See application file for complete search history.

(56) References Cited

FOREIGN PATENT DOCUMENTS

| CN | 108384767 A | 8/2018 |
| JP | 2008522627 A | 7/2008 |
| WO | 2006063336 | 6/2006 |
| WO | 2014037376 | 3/2014 |
| WO | 2016075082 | 5/2016 |
| WO | 2016198660 | 12/2016 |
| WO | 2016198665 | 12/2016 |
| WO | 2019095161 A1 | 5/2019 |

OTHER PUBLICATIONS

Gao X, Wei P. [Advances in molecular modification of ω-transaminase]. Sheng wu Gong Cheng xue bao=Chinese Journal of Biotechnology. Jul. 2018;34(7):1057-1068.

Zhu WL, Hu S, Lv CJ, et al. A Single Mutation Increases the Thermostability and Activity of Aspergillus terreus Amine Transaminase. Molecules. 2019;24(7):1194.

Martin, A. R., et al., "Improved activity and thermostability of (S)-aminotransferase by error-prone polymerase chain reaction for teh production of a chiral amine," Biochemical Engineering Journal, vol. 37 (2007), pp. 246-255.

Van Oosterwijk, N., et al., "Structural Basis of the Substrate Range and Enantioselectivity of Two (S)-Selective [omega]-Transaminases," Biochemistry, vol. 55, No. 31 (2016), pp. 4422-4431.

*Primary Examiner* — Tekchand Saidha
(74) *Attorney, Agent, or Firm* — Riverside Law LLP

(57) ABSTRACT

Provided are a transaminase mutant and a method for producing a chiral amine using the same. An amino acid sequence of the transaminase mutant is an amino acid sequence obtained by mutation occurred in an amino acid sequence as shown in SEQ ID NO: 1, and the mutation includes at least one of the following mutation sites: position 3, position 5, position 8, position 25, position 32, position 45, position 56, position 59, position 60, position 84, position 86, position 164, position 176, position 178, position 180, position 187, position 197, position 206, position 207, position 242, position 245, position 319 and position 324.

19 Claims, 1 Drawing Sheet
Specification includes a Sequence Listing.

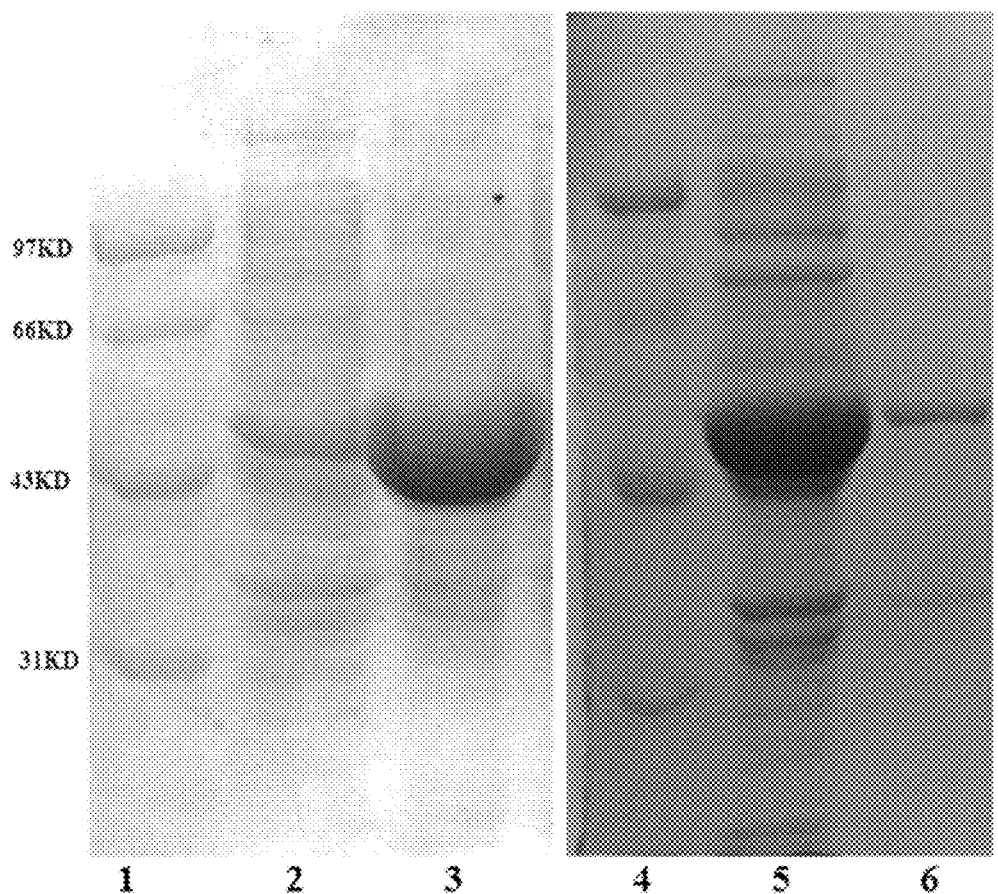

TRANSAMINASE MUTANT AND USE THEREOF

CROSS-REFERENCE TO RELATED APPLICATIONS

This application is a U.S. National Phase application filed under 35 U.S.C. § 371 claiming benefit to International Patent Application No. PCT/CN2019/089170, which was filed on May 30, 2019, the entire contents of which are incorporated herein by reference in its entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206418-0005-00US_Sequence_Listing_ST25.txt" in ASCII format. The text file containing the Sequence Listing of the present application was created on Nov. 30, 2021, is 4,522 bytes in size, and is identical to the Sequence Listing filed in corresponding International Patent Application No. PCT/CN2019/089170, filed on May 30, 2019.

TECHNICAL FELD

The disclosure relates to the field of biotechnologies, and in particular, to a transaminase mutant and use thereof.

BACKGROUND

Chiral amines widely exist in the natural world, and are important intermediates for synthesizing natural products and chiral drugs. Many chiral amines contain one or more chiral centers, there are significant differences in pharmacological activity, metabolic process, metabolic rate and toxicity of the different chiral drugs, usually one enantiomer is effective, but the other enantiomer is low-effective or ineffective, and even toxic. Therefore, how to efficiently and stereoselectively construct compounds containing the chiral centers is of great significance in pharmaceutical research and development.

The chiral amines are an important composition part for synthesizing a variety of biologically active compounds and active pharmaceutical ingredients. It is estimated that 40% of existing drugs are the chiral amines and derivatives thereof, for example, the synthesis of neurological drugs, cardiovascular drugs, antihypertensive drugs, anti-infective drugs and vaccines all uses the chiral amines as intermediates (Top. Catal. 2014, 57, 284-300), this makes chiral amine compounds become an important part of a pharmaceutical industry.

There are many types of industrial production for the chiral amines, it mainly relies on metal-catalyzed hydrogenation of an enamide from a ketone precursor, and a process requires expensive transition metal complexes as catalysts. Because these transition metal complex resources are limited, it is difficult to achieve sustainability. At the same time, the process of asymmetric-synthesizing the chiral amine from the ketone precursor requires protection and deprotection steps of an amine, steps and waste are increased, and a yield is reduced.

In a method of synthesizing the chiral amine by a catalytic hydrogenation reduction, the catalyst is difficult in preparation and expensive, the device investment is large, the production cost is high, the requirements for activity of catalyst and hydrogenation performances are very high, and the catalyst is toxic, especially a sulfide in hydrogen, it easily causes a person to be poisoned.

Transaminase is a generic term of enzymes that use pyridoxal phosphate as a cofactor, and catalyze an amino on 1 amino donor (amino acid or amine) to be transferred to a prochiral acceptor ketone, as to obtain a chiral amine or a by-product ketone or α-keto acid thereof. Because traditional chemical methods for asymmetric-synthesizing amines have different limitations, such as low efficiency, low selectivity and serious environmental pollution, at the same time, the synthesis of the chiral amines catalyzed by the transaminase has high stereo and chemoselectivity, has safety and environmental compatibility, and is a process of green environmental protection, it is called green chemistry. At the same time, enzyme catalysis is often in place in one step, it has incomparable advantages of the chemical methods. The synthesis of the chiral compounds by the transaminase becomes a key asymmetric synthesis technology.

Although the progress of using the transaminase to produce the chiral amines is highly concerned, an enzymatic method has many problems in amplified production application. For example, the increase of a fermentation cost is caused by low enzyme activity and large amount of enzymes; at the same time, the large amount of the enzymes caused by the low enzyme activity seriously hinders an industrial application of an enzyme-catalyzed reaction. On the one hand, the large amount of the enzymes causes that a reaction volume is large, and a utilization rate of a catalytic container is reduced. At the same time, it is caused that a volume of post-treatment is increased, and an amount of an extraction solvent is large, so that extraction, concentration and acquisition of a product are difficult, and a product yield is low, it greatly hinders the industrial application of the enzyme catalysis. Enzymes with high activity may reduce the amount of the enzymes and the reaction volume, so that the industrial application of the enzyme catalysis is possible. Therefore, it is very important to obtain the high-activity enzymes. At the same time, a substrate spectrum of the enzymes may also be expanded, so that some enzyme-catalyzed reactions with extremely low conversion rates or even inactivity may proceed smoothly, an excellent conversion rate and an extremely high product chiral purity are achieved.

On the other hand, while catalyzed, the enzyme is easily affected by an organic solvent in a reaction system or easily affected to be denatured and inactivated by factors, such as high pH and high temperature of the reaction. Therefore, it is also critical that the tolerance of the enzyme to extreme conditions is increased. In the industrial production of the chiral amines, because most of existing substrates and amino donors are poorly water-soluble, in order to increase the production of chiral amine products, it is necessary to increase the content of the organic solvents in the reaction system, or use basic amino donors (such as isopropylamine), an extremely harsh reaction condition is created, so that wild transaminase is extremely easily denatured to lose activity, so the transaminase that is well tolerant to the organic solvent and high pH is required to meet the needs of the industrial production.

SUMMARY

The disclosure aims to provide a transaminase mutant and use thereof, as to improve activity of transaminase.

In order to achieve the above purpose, according to one aspect of the disclosure, a transaminase mutant is provided. An amino acid sequence of the transaminase mutant is an amino acid sequence obtained by mutation occurred in an amino acid sequence as shown in SEQ ID NO: 1, and the mutation includes at least one of the following mutation sites: position 3, position 5, position 8, position 25, position 32, position 45, position 56, position 59, position 60, position 84, position 86, position 164, position 176, position 178, position 180, position 187, position 197, position 206, position 207, position 242, position 245, position 319, position 324, position 326, position 328, position 370, position 397, position 414, position 416, position 424, position 436, position 437 and position 442.

Further, the amino acid sequence of the transaminase mutant is an amino acid sequence obtained by mutation occurred in the amino acid sequence as shown in SEQ ID NO:1, and the mutation includes at least one of the following mutation sites: L3S, V5S, I8A, I8S, F25L, F25T, Q32N, I45W, L59V, F56M, C60F, C60Y, F84V, W86H, W86L, W86P, W86N, F164M, F164V, F176Y, F176S, A178L, I180V, S187A, T197P, L206M, K207T, V242A, T245A, T245V, R319C, R324A, R324G, E326M, V328A, V328G, L370A, L370D, L370K, T397A, P414G, Q416A, E424D, E424T, A436S, A436G, A436P, A436N, A436Y, A436Q, A436E, M437S, M437A, R442T, R442S, R442Q and R442V; or an amino acid sequence of the transaminase mutant has the mutation sites in the mutated amino acid sequence, and has more than 80% identity with the mutated amino acid sequence.

Further, the mutation further includes at least one of the following mutation sites: C60Y+F164V, L3S+V5S, L3S+V5S+F164V, L3S+V5S+C60Y, L3S+V5S+C60Y+F164V, I180V+L370A and L3S+V5S+L59V; preferably, the mutation further includes at least one of the following mutation site combinations: F164V+C60Y, E424D+A436G, C60Y+F164V+A436P, C60Y+F164V+A436N, W86P+F164V, F25L+L59V, F25T+F164V, C60Y+F164V+A436Y, C60Y+F164V+A436Q, C60Y+F164V+A436E, F164V+M437A, I8A+V328A, I8S+F164V, C60Y+F164V+L370A, C60Y+F164V+L370D, C60Y+F164V+L370K, I45W+F164V, C60Y+F164V+F176Y, C60Y+F176S+F164V, L3S+V5S+C60Y+F164V+L370A, C60Y+F164V+R442S, C60Y+F164V+R442Q, L3S+V5S+S187A+L370A+E424D, C60Y+F164V+R442T, L3S+V5S+E424D+L370A, L3S+V5S+F164V+C60Y+I180V+L370A, L3S+V5S+C60Y+F164V+A178L+L370A, L3S+V5S+F164V+T197P+L370A, L3S+V5S+V328A+E424D, L3S+V5S+L59V+L206M+L370A, L3S+V5S+L370A+E424D, L3S+V5S+F164V+K207T+L370A, L3S+V5S+S244A+L370A, L3S+V5S+F164V+T245A+L370A, L3S+V5S+F164V+T245V+V328A, L3S+V5S+F164V+L370A+T397A, L3S+V5S+L59V+F164V+R319C+L370A+T397A, L3S+V5S+L59V+F164V+L370A, L3S+V5S+L59V+L370A+A436G+Q416A, L3+V5S+L59V+L370A+A436G+R442Q, L3S+V5S+L59V+V328A+L370A+R442Q, L3S+V5S+L59V+L370A+R442L, L3S+V5S+L59V+C60Y+F164V+L370A+R442V, L3S+V5S+C60Y+F164V+A178L+S187A+I180V+L370A, and L3S+V5S+C60Y+F164V+I180V+S187A+L370A+R442L.

Further, the mutation at least includes one of the following mutation sites or mutation site combinations: position 7, position 32, position 96, position 164, position 171, position 186, position 252, position 384, position 389, position 391, position 394, position 404, position 411, position 420, position 423, position 424, position 442, position 452 and position 456; preferably, the mutation at least also includes one of the following mutation sites: K7N, Q32L, K96R, V164L, E171D, S186G, V252I, Y384F, I389M, I389F, D391E, N394D, L404Q, L404Q, G411D, Q420R, Q420K, M423K, E424R, E424K, E424Q, R442H, R442L, G452S and K456R.

Further, the mutation at least includes one of the following mutation site combinations: L3S+V5S+C60Y+F164V+A178L+S187A+I180V+L370A+Y384F+G452S, L3S+V5S+C60Y+F164V+A178L+S187A+I180V+L370A+S186G+Q420R, L3S+V5S+C60Y+F164V+A178L+S187A+I180V+L370A+M423K, L3S+V5S+C60Y+F164V+A178L+S187A+I180V+L370A+Q420K+E424R, L3S+V5S+C60Y+F164V+A178L+S187A+I180V+L370A+K7N+E424Q, L3S+V5S+C60Y+F164V+A178L+S187A+I180V+L370A+D391E, L3S+V5S+C60Y+F164V+A178L+S187A+I180V+L370A+Q32L+E171D, L3S+V5S+C60Y+F164V+A178L+S187A+I180V+L370A+I389M, L3S+V5S+C60Y+F164V+A178L+S187A+I180V+L370A+I389F+N394D, L3S+V5S+C60Y+F164V+A178L+S187A+I180V+L370A+L404Q, L3S+V5S+C60Y+F164V+A178L+S187A+I180V+L370A+I389F+L404Q, L3S+V5S+C60Y+F164V+A178L+S187A+I180V+L370A+V164L+K456R, L3S+V5S+C60Y+F164V+A178L+S187A+I180V+L370A+K96R, L3S+V5S+C60Y+F164V+A178L+S187A+I180V+L370A+Q32L+R442H, L3S+V5S+C60Y+F164V+A178L+S187A+I180V+L370A+R442L, L3S+V5S+C60Y+F164V+A178L+S187A+I180V+L370A+V252I, L3S+V5S+C60Y+F164V+A178L+S187A+I180V+L370A+E424K, L3S+V5S+C60Y+F164V+A178L+S187A+I180V+L370A, L3S+V5S+C60Y+F164V+Q420R+L370A, L3S+V5S+F164V+C60Y+L370A+G452S, L3S+V5S+C60Y+F164V+A178L+S187A+I180V+L370A+G411D+E424K, L3S+V5S+C60Y+F164V+A178L+S187A+I180V+L370A+Y384F+L404Q, L3S+V5S+C60Y+F164V+A178L+S187A+I180V+L370A+E424K+G411D, L3S+V5S+C60Y+F164V+A178L+S187A+I180V+L370A+G411D+S186G, L3S+V5S+C60Y+F164V+A178L+S187A+I180V+L370A+S186G+Q420R, L3S+V5S+C60Y+F164V+A178L+S187A+I180V+L370A+G411D, L3S+V5S+C60Y+F164V+A178L+S187A+I180V+L370A+G411D+V164L+I389F+E424Q+K96R, L3S+V5S+C60Y+F164V+A178L+S187A+I180V+L370A+V164L+I389F+L404Q, L3S+V5S+C60Y+F164V+A178L+I180V+L370A+G411D+M423K, L3S+V5S+C60Y+F164V+A178L+S187A+I180V+L370A+G411D+S186G+I389F+L404Q, L3S+V5S+C60Y+F164L+A178L+S187A+I180V+L370A+G411D+S186G+Y384F, L3S+V5S+C60Y+F164V+A178L+S187A+I180V+L370A+G411D+S186G+Y384F+V164L+E171D, L3S+V5S+C60Y+F164V+A178L+S187A+I180V+L370A+G411D+S186G+Y384F+I389F+L404Q, L3S+V5S+C60Y+F164L+A178L+S187A+I180V+L370A+G411D+S186G+Y384F+V252I, L3S+V5S+C60Y+F164L+A178L+S187A+I180V+L370A+G411D+S186G+Y384F+I389F+V252I, L3S+V5S+C60Y+F164L+A178L+S187A+I180V+L370A+G411D+S186G+Y384F+E424Q, L3S+V5S+C60Y+F164L+A178L+S187A+I180V+L370A+G411D+S186G+Y384F+I389F, L3S+V5S+C60Y+F164L+A178L+S187A+I180V+L370A+G411D+S186G+Y384F+I389F+V252I+L404Q, L3S+V5S+C60Y+F164L+A178L+S187A+I180V+L370A+G411D+S186G+Y384F+I389F+V252I+E424Q, L3S+V5S+C60Y+F164L+A178L+S187A+I180V+L370A+G411D+S186G+Y384F+I389F+V252I+L404Q+E171D, L3S+V5S+C60Y+F164L+A178L+

S187A+I180V+L370A+G411D+S186G+Y384F+I389F+
V252I+E424Q+M423K, L3S+V5S+C60Y+F164L+
A178L+S187A+I180V+L370A+G411D+S186G+Y384F+
I389F+V252I+L404Q+E171D+D391E, L3S+V5S+C60Y+
F164V+A178L+S187A+I180V+L370A+G411D+S186G+
Y384F+E424Q+K7N, L3S+V5S+C60Y+F164V+A178L+
S187A+I180V+L370A+G411D+S186G+Y384F+E171D,
L3S+V5S+C60Y+F164V+A178L+S187A+I180V+
L370A+G411D+S186G+Y384F+D391E, L3S+V5S+
C60Y+F164V+A178L+S187A+I180V+L370A+G411D+
S186G+Y384F, L3S+V5S+C60Y+F164V+I180V+L370A+
G411D+R442L, C60Y+F164L+I180V+L370A+G411D+
A178L+S186G+S187A+Y384F+E171D+I389F+V252I+
L404Q, C60Y+F164V+I180V+L370A+G411D+A178L+
S186G+S187A+Y384F+E424Q, L3S+V5S+C60Y+
F164V+A178L+S187A+I180V+L370A+G411D, C60Y+
F164V+R442Q+G411D, L3S+V5S+F164V+C60Y+
I180V+L370A+G411D, L3S+V5S+C60Y+F164V+
L370A+G411D, L3S+V5S+C60Y+F164V+Q420R+
L370A+G411D, C60Y+F164V+L370A+G411D, L3S+
V5S+F164V+C60Y+L370A+G452S+G411D+Y384F,
C60Y+F164V+R442Q+Y384F, L3S+V5S+F164V+C60Y+
I180V+L370A+Y384F, L3S+V5S+C60Y+F164V+L370A+
Y384F, L3S+V5S+C60Y+F164V+Q420R+L370A+Y384F,
C60Y+F164V+L370A+Y384F, L3S+V5S+F164V+C60Y+
L370A+G452S+Y384F, C60Y+F164V+R442Q+S186G,
L3S+V5S+F164V+C60Y+I180V+L370A+S186G, L3S+
V5S+C60Y+F164V+L370A+S186G, L3S+V5S+C60Y+
F164V+Q420R+L370A+S186G, C60Y+F164V+L370A+
S186G, L3S+V5S+F164V+C60Y+L370A+G452S+S186G,
C60Y+F164V+R442Q+D391E, L3S+V5S+F164V+C60Y+
I180V+L370A+D391E, L3S+V5S+C60Y+F164V+L370A+
D391E, L3S+V5S+C60Y+F164V+Q420R+L370A+D391E,
C60Y+F164V+L370A+D391E, L3S+V5S+F164V+C60Y+
L370A+G452S+D391E, C60Y+F164V+R442Q+E171D,
L3S+V5S+F164V+C60Y+I180V+L370A+E171D, L3S+
V5S+C60Y+F164V+L370A+E171D, L3S+V5S+C60Y+
F164V+Q420R+L370A+E171D, C60Y+F164V+L370A+
E171D, L3S+V5S+F164V+C60Y+L370A+G452S+E171D,
C60Y+F164V+R442Q+L404Q, L3S+V5S+F164V+C60Y+
I180V+L370A+L404Q, L3S+V5S+C60Y+F164V+L370A+
L404Q, L3S+V5S+C60Y+F164V+Q420R+L370A+L404Q,
C60Y+F164V+L370A+L404Q, and L3S+V5S+F164V+
C60Y+L370A+G452S+L404Q.

According to another aspect of the disclosure, a DNA molecule is provided. The DNA molecule encodes any one of the above transaminase mutants.

According to another aspect of the disclosure, a recombinant plasmid is provided. The recombinant plasmid contains any one of the above DNA molecules.

Further, the recombinant plasmid is pET-22a(+), pET-22b(+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

According to another aspect of the disclosure, a host cell is provided. The host cell contains any one of the above recombinant plasmids.

Further, the host cell includes prokaryotic cell, yeast or eukaryotic cell; preferably, the prokaryotic cell is *Escherichia coli* BL21-DE3 cell or *Escherichia coli* Rosetta-DE3 cell.

According to another aspect of the disclosure, a method for producing a chiral amine is provided. The method includes a step of using a transaminase to catalyze a transamination reaction of a ketone compound and an amino donor, wherein the transaminase is any one of the above transaminase mutants.

Further, the ketone compound is

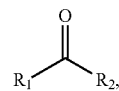

$R_1$ and $R_2$ are each independently optionally substituted or unsubstituted alkyl, optionally substituted or unsubstituted aralkyl, or optionally substituted or unsubstituted aryl; and $R_1$ and $R_2$ can form a substituted or unsubstituted ring alone or in combination;

preferably, $R_1$ and $R_2$ are optionally substituted or unsubstituted alkyl, optionally substituted or unsubstituted aralkyl, or optionally substituted or unsubstituted aryl having 1 to 20 carbon atoms, more preferably optionally substituted or unsubstituted alkyl, optionally substituted or unsubstituted aralkyl group, or optionally substituted or unsubstituted aryl having 1 to 10 carbon atoms;

preferably, the aryl includes phenyl, naphthyl, pyridyl, thienyl, oxadiazole group, imidazole group, thiazolyl, furanyl, pyrrolyl, phenoxy, naphthyloxy, pyridyloxy, thienyloxy, oxadiazoloxy, imidazoloxy, thiazolyloxy, furanyloxy and pyrrolyloxy;

preferably, the alkyl includes methyl, ethyl, propyl, butyl, pentyl, hexyl, isopropyl, sec-butyl, t-butyl, methoxy, ethoxy, t-butoxy, methoxy carbonyl, ethoxy carbonyl, t-butoxy carbonyl, vinyl, allyl, cyclopentyl and cycloheptyl;

preferably, the aralkyl is a benzyl; and preferably, the substitution refers to substitution with halogen atom, nitrogen atom, sulfur atom, hydroxy, nitro, cyano, methoxy, ethoxy, carboxyl, carboxymethyl, carboxyethyl or methylenedioxy.

Preferably, the ketone compound is

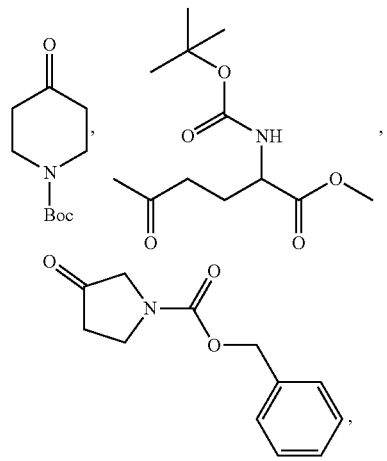

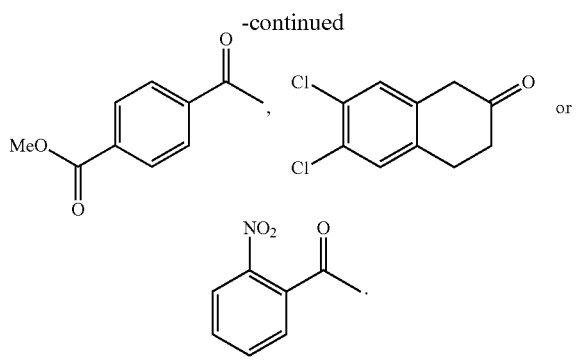

Further, the amino donor is isopropylamine or alanine, preferably the isopropylamine.

Further, in a reaction system the transaminase catalyzes the transamination reaction of the ketone compound and the amino donor, the pH is 7 to 11, preferably 8 to 10, and more preferably 9 to 10.

Further, in the reaction system the transaminase catalyzes the transamination reaction of the ketone compound and the amino donor, the temperature is 25° C. to 60° C., more preferably 30 to 55° C., and further preferably 40 to 50° C.

Further, a volume concentration of dimethyl sulfoxide in the reaction system the transaminase catalyzes the transamination reaction of the ketone compound and the amino donor is 0% to 50%.

Further, the volume concentration of methyl tert-butyl ether in the reaction system the transaminase catalyzes the transamination reaction of the ketone compound and the amino donor is 0% to 90%.

The above transaminase mutants of the disclosure are based on the transaminase shown in SEQ ID NO: 1, and are mutated through a site-directed mutation method, thereby the amino acid sequence thereof is changed, so changes in protein structure and function are achieved, and through a directed screening method, the transaminase with the above mutation sites is obtained. Therefore, these transaminase mutants have good organic solvent tolerance and high pH tolerance, and have high soluble expression characteristics and high activity characteristics, a reaction rate may be improved by use of these mutants, the enzyme stability is improved, the amount of the enzyme is reduced, and the difficulty of post-treatment is reduced, so it may be suitable for industrial production.

BRIEF DESCRIPTION OF THE DRAWINGS

Drawings for constituting a part of the present disclosure are used to provide further understanding of the disclosure. Exemplary embodiments of the disclosure and descriptions thereof are used to explain the disclosure, and do not constitute improper limitation to the disclosure. In the drawings:

FIG. 1 shows an electrophoresis diagram of an expression condition of a protein detected by SDS-PAGE in an embodiment of the disclosure.

DETAILED DESCRIPTION OF THE EMBODIMENTS

It is to be noted that embodiments in the present disclosure and features in the embodiments may be combined with each other in the case without conflicting. The disclosure is described in detail below in combination with the embodiments.

Transaminase is a type of protein-based biocatalysts. In an industrial production process, certain organic solvent, pressure, pH and other conditions that are easy to denature a protein are often required. Therefore, the biocatalyst used needs to have high tolerance in order to meet the needs of the industrial production. However, wild transaminase often has low tolerance to industrial demand conditions, thereby its wide application is limited.

Transaminase ArS-ωTA derived from *Arthrobacter citreus* may specifically catalyze a ketone compound to produce an amino product, but an enzyme has low tolerance to the organic solvent, and the enzyme has low tolerance in high pH. At the same time, the enzyme is poor in soluble expression in a prokaryotic expression system, and the enzyme has low activity to a substrate, so that a usage amount of the enzyme is larger, and the ketone compound is converted less; at the same time, due to the large amount of the enzyme, the difficulty of post-treatment is also increased, a yield is low, and a process is complicated. The disclosure performs modification in allusion to the above disadvantages of the transaminase ArS-ωTA, its organic solvent tolerance is improved, pH tolerance, soluble expression characteristics and activity characteristics are improved, so that it may be applied to industrial production conditions.

Rational modification of the enzyme is based on a three-dimensional molecular structure of the enzyme to modify a substrate binding site, a coenzyme binding site, a surface and other parts of the enzyme, as to change catalytic properties of the enzyme and improve the characteristics, such as activity and selectivity, of the enzyme. Directed evolution of the enzyme is a non-rational design of the protein, a special evolutionary condition is artificially created, a natural evolutionary mechanism is simulated, a gene is modified in vitro, and error-prone PCR, DNA shuffling and other technologies are applied, a new enzyme with expected properties is obtained in combination with an efficient screening system.

A technical scheme of the disclosure rationally modifies the ArS-ωTA protein through a technology combined with rational design and random mutation, the obtained mutant uses the ketone compound for activity verification, and finally a mutant strain having good organic solvent tolerance, high pH tolerance, soluble expression, activity and selectivity is obtained.

The rational design may be performed by means of site-directed mutation. Herein, the site-directed mutation: means that a desired change (usually a change representing a favorable direction) is introduced into a target DNA fragment (may be a genome or a plasmid) by a polymerase chain reaction (PCR) and other methods, including base addition, deletion, point mutation and the like. The site-directed mutation may quickly and efficiently improve characters and representation of a target protein expressed by DNA, and is a very useful method in gene research.

The method of introducing the site-directed mutation using a whole-plasmid PCR is simple and effective, and is a more commonly used method at present. A principle is that a pair of primers (forward and reverse) containing mutation sites are annealed with a template plasmid, and "circularly extended" by a polymerase. The so-called cyclic extension means that the polymerase extends the primer according to the template, and then returns to a 5'-end of the primer to be terminated after one round, and it undergoes circulation of repeated heating and annealing extension, this reaction is different from rolling circle amplification and does not form multiple tandem copies. Extension products of the forward and reverse primers are annealed and matched to form an open-circle plasmid with a nick. The extension product of Dpn I digestion, because the original template plasmid is derived from conventional *Escherichia coli*, is modified by dam methylation, and is fragmented because it is sensitive to Dpn 1, the plasmid with a mutation sequence synthesized in vitro is not digested because it is not methylated, so it may be successfully transformed in the subsequent transformation, and a clone of the mutant plasmid may be obtained.

The above mutant plasmid is transformed into an *Escherichia coli* cell, and overexpressed in the *Escherichia coli*. Then, a crude enzyme is obtained by ultra-sonicating the cells. The optimum conditions for induction expression of the transaminase: 25° C., and 0.1 mM IPTG induction overnight.

Through computer simulation analysis of a three-dimensional structure of the transaminase using software, it is found that the ArS-ωTA protein is an S-type transaminase with pyridoxal 5-phosphate (PLP) as a cofactor. An amino acid near the active center of the enzyme is modified to improve its enzymatic properties, such as stabilizing a transition state, reducing free energy of a binding state between the enzyme and a reaction transition state molecule, making the substrate more easily enter the active neutrality, and reducing the steric hindrance of the substrate; and an amino acid far away from the active center is modified, chemical bond that promotes the stability, such as hydrogen bond, disulfide bond, salt bridge and hydrophobic accumulation, is added, so the stability of the protein may be improved, and a protein half-life is increased.

The disclosure rationally modifies the ArS-ωTA protein (SEQ ID NO: 1) and performs amino acid mutations (L3S, V5S, I8A, I8S, I45W, F25L, F25T, Q32N, L59V, F56M, C60F, C60Y, F84V, W86H, W86L, W86P, W86N, Y89F, F164M, F164V, F164Y, F176Y, F176S, A178L, I180V, S187A, T197P, L206M, K207T, T245A, T245V, R319C, V242A, V328A, V328G, T397A, P414G, E424D, E424T, L370A, L370D, L370K, R324A, R324G, E326M, Q416A, A436S, A436G, A436P, A436N, A436Y, A436Q, A436E, M437S, M437A, R442T, R442S, R442Q, R442V, R442A) and combination mutations thereof, preferably pET22b is used as an expression vector, and a plasmid containing a mutant gene is obtained, preferably BL21 (DE3) is used as an expression strain, and the mutant protein is obtained under the induction of IPTG.

The constructed mutant protein performs activity verification, and results are shown in Table 1:

TABLE 1

Table 1: Strain

| | Amino acid difference (compare to ArS-ωTA) | multiple of activity increased (compare to ArS-ωTA) |
|---|---|---|
| ArS-ωTA | N/A | 0 |
| M1 | I8A | 0.91 |
| M2 | I8S | 2.15 |
| M3 | Q32N | 2.25 |
| M4 | F56M | 5.3 |
| M5 | L59V | 4.73 |
| M6 | C60F | 15.1 |
| M7 | F84V | 2.98 |
| M8 | W86H | 5.51 |
| M9 | W86L | 3.93 |
| M10 | W86P | 5.6 |

TABLE 1-continued

Table 1: Strain

| | Amino acid difference (compare to ArS-ωTA) | multiple of activity increased (compare to ArS-ωTA) |
|---|---|---|
| M11 | W86N | 0.6 |
| M12 | Y89F | −0.1 |
| M13 | F164M | 14.5 |
| M14 | F164V | 45.1 |
| M15 | V242A | 11.7 |
| M16 | V328A | 6.56 |
| M17 | V328G | 2.84 |
| M18 | P414G | 8.31 |
| M19 | E424D | 5.29 |
| M20 | E424T | 6.58 |
| M21 | A436S | 5.5 |
| M22 | A436V | 9.6 |
| M23 | R442V | −1 |
| M24 | R442A | −1 |
| M25 | L3S + V5S | 0.20 |
| M26 | C60Y | 30.17 |
| M27 | F164Y | −0.2 |
| M28 | A436G | 3.67 |

Multiple sites that may improve the catalytic activity of the transaminase mutants are obtained above through the site-directed mutation. The activity verification is performed by using 10 wt of wet weight cells at 0.02 g/ml of the substrate concentration, and the activity of the optimal mutant obtained is 4 (times greater than that of the parent ArS-ωTA. However, the activity of the original bacteria ArS-ωTA is too low, the mutant after the 45-time increase of the activity still has a large amount of the substrate that may not be converted into amino products after 16 hours of the conversation. Therefore, further modification is carried out, including introduction of beneficial site combinations and new mutation sites, the mutant after the modification is subjected to the activity verification using 5 wt~0.5 wt of the weight cells at 0.1 g/ml of the substrate concentration, as shown in Table 2.

TABLE 2

| Strain | Amino acid difference (compare to ArS-ωTA) | Multiple of activity increased (compare to ArS-ωTA) |
|---|---|---|
| M29 | F164V + C60Y | 105.3 |
| M30 | E424D + A436G | 107.3 |
| M31 | C60Y + F164V + A436P | 116.3 |
| M32 | C60Y + F164V + A436N | 55.3 |
| M33 | W86P + F164V | 1 |
| M34 | F25L + L59V | 47.2 |
| M35 | F25T + F164V | 0.6 |
| M36 | C60Y + F164V + A436Y | 140 |
| M37 | C60Y + F164V + A436Q | 144.07 |
| M38 | C60Y + F164V + A436E | 66 |
| M39 | V328A + M437S | −1 |
| M40 | F164V + M437A | 0.5 |
| M41 | I8A + V328A | 135.4 |
| M42 | I8S + F164V | 14.1 |
| M43 | C60Y + F164V + L370A | 199.4 |
| M44 | C60Y + F164V + L370D | 203.4 |
| M45 | C60Y + F164V + L370K | 165.1 |
| M46 | I45W + F164V | 0.1 |
| M47 | C60Y + F164V + F176Y | 164.5 |
| M48 | C60Y + F176S + F164V | 159.3 |
| M49 | F164V + R324A | −1 |
| M50 | F164V + R324G | −1 |
| M51 | E326M + E424T | 0 |
| M52 | L3S + V5S + C60Y + F164V + L370A | 238.9 |
| M53 | C60Y + F164V + R442S | 1004.1 |

TABLE 2-continued

| Strain | Amino acid difference (compare to ArS-ωTA) | Multiple of activity increased (compare to ArS-ωTA) |
|---|---|---|
| M54 | C60Y + F164V + R442Q | 2526.6 |
| M55 | L3S + V5S + S187A + L370A + E424D | 1274.6 |
| M56 | C60Y + F164V + R442T | 567.7 |
| M57 | L3S + V5S + E424D + L370A | 858.6 |
| M58 | L3S + V5S + F164V + C60Y + I180V + L370A | 2655.4 |
| M59 | L3S + V5S + C60Y + F164V + A178L + L370A | 2467.4 |
| M60 | L3S + V5S + F164V + T197P + L370A | 16.5 |
| M61 | L3S + V5S + V328A + E424D | 1089.9 |
| M62 | L3S + V5S + L59V + L206M + L370A | 1357.9 |
| M63 | L3S + V5S + L370A + E424D | 630.6 |
| M64 | L3S + V5S + F164V + K207T + L370A | 807 |
| M65 | L3S + V5S + S244A + L370A | 1189.2 |
| M66 | L3S + V5S + F164V + T245A + L370A | 13.9 |
| M67 | L3S + V5S + F164V + T245V + V328A | 23.4 |
| M68 | L3S + V5S + F164V + L370A + T397A | 281.2 |
| M69 | L3S + V5S + L59V + F164V + R319C + L370A + T397A | 20.8 |
| M70 | L3S + V5S + L59V + F164V + L370A | 5.2 |
| M71 | L3S + V5S + L59V + L370A + A436G + Q416A | 1725.9 |
| M72 | L3 + V5S + L59V + L370A + A436G + R442Q | 620.8 |
| M73 | L3S + V5S + L59V + V328A + L370A + R442Q | 1671 |
| M74 | L3S + V5S + L59V + L370A + R442L | 2343.4 |
| M75 | L3S + V5S + L59V + C60Y + F164V + L370A + R442V | 1121.9 |
| M76 | L3S + V5S + C60Y + F164V + A178L + S187A + I180V + L370A | 3455.4 |
| M77 | L3S + V5S + C60Y + F164V + I180V + S187A + L370A + R442L | 3200.8 |

After the above modification, multiple sites that may improve the catalytic activity of the transaminase mutant are obtained, and a beneficial mutation combination is carried out at the same time, and multiple mutation site combinations with the improved activity are obtained. The activity of the best strain is 3455 times greater than that of the ArS-ωTA. The optimal mutant strain is subjected to the activity verification using 0.5 wt of wet weight cells at 0.1 g/ml of the substrate concentration in a reaction system (a volume is very small, 10 V). After 16 hours of the conversation, a conversation rate reaches more than 95%.

It may be seen that the mutant strain is excellently improved in catalytic activity, and improved from the basic non-catalytic activity of the wild bacteria (10 wt of the wet weight cells, 0.02 g/ml of the substrate concentration, and 0.1% of the conversion rate), to the excellent catalytic activity: a very small amount of the enzyme (0.5 wt) and a very small reaction volume (10 V) are used to achieve 95% of a conversion effect.

The disclosure simultaneously performs directed evolution on the above mutant protein obtained by the rational modification, and a mutant protein that greatly improves (improvement of quality) the activity of the ketone substrate is obtained. This mutant protein is used as an original strain, error-prone PCR is used as a technical means to process random mutations, as to further improve its activity and characteristics such as organic solvent tolerance and high pH tolerance. At the same time, combined with a site-directed mutation technology and a staggered extension PCR random recombination technology, the beneficial mutations obtained by the error-prone PCR are continuously accumulated. The obtained mutants construct a mutant library containing the random mutations, the organic solvent concentration is continuously increased, the pH of the screening and reaction system is continuously increased, and a screening pressure is set, to obtain a target property mutant. The mutant uses pET22b as an expression vector and uses BL21 (DE3) as an expression strain, and the mutant protein is obtained under the induction of IPTG. The induced mutant strains containing the target protein are lysed by an ultrasonication mode to release the target protein, and an expression condition of the target protein is detected by SDS-PAGE.

Herein, the error-prone PCR is to change a mutation frequency in an amplification process by adjusting reaction conditions while a DNA polymerase is used to amplify a target gene, the tendency of an inherent mutation sequence of the polymerase is reduced, and the diversity of a mutation spectrum is increased, so that wrong bases are randomly incorporated into the amplified gene at a certain frequency, thereby a randomly mutated DNA group is obtained.

In the disclosure, a variety of the mutations are obtained by the above method of random mutation and directed screening, and through the activity verification, the mutant improves the tolerance to the organic solvent, the tolerance to the pH, the activity to the substrate, and the solubility of the target protein.

Tolerance verification: a tolerance improvement degree of the mutation site obtained by the error-prone PCR in 35% of dimethyl sulfoxide Tolerance verification results of a beneficial mutation site obtained using M76 (L3S+V5S+C60Y+F164V+A178L+S187A+I180V+L370A) as the original strain in 35% of the dimethyl sulfoxide are shown in Table 3.

TABLE 3

| Strain | Amino acid difference (compare to M76) | Tolerance improvement degree |
|---|---|---|
| M76 | N/A | Null |
| M78 | G411D | 225.83% |
| M79 | Y384F + G452S | 218.95% |
| M80 | S186G + Q420R | 554.20% |
| M81 | M423K | 150.10% |
| M82 | Q420K + E424R | 183.15% |
| M83 | K7N + E424Q | 83.33% |
| M84 | D391E | 401.29% |
| M85 | Q32L + E171D | 594.07% |
| M86 | I389M | 335.16% |
| M87 | I389F + N394D | 37.76% |
| M88 | L404Q | 12.06% |
| M89 | I389F + L404Q | 137.91% |
| M90 | V164L + K456R | 351.86% |
| M91 | K96R | 23.48% |
| M92 | Q32L + R442H | 131.25% |
| M93 | R442L | 157.16% |
| M94 | V252I | 131.58% |
| M95 | E424K | 59.79% |

Tolerance versification: a tolerance improvement degree of the mutation site obtained by the error-prone PCR in 50% of methyl tert-butyl ether.

Tolerance verification results of a beneficial mutation site obtained using M76 (L3S+V5S+C60Y+F164V+A178L+S187A+I180V+L370A) as the original strain in 50% of the methyl tert-butyl ether are shown in Table 4.

TABLE 4

| Strain | Amino acid difference (compare to M76) | Tolerance improvement degree |
|---|---|---|
| M76 | N/A | Null |
| M78 | G411D | 26.22% |
| M79 | Y384F + G452S | 27.56% |
| M80 | S186G + Q420R | 63.70% |
| M81 | M423K | 350.13% |
| M82 | Q420K + E424R | 443.27% |
| M83 | K7N + E424Q | 17.87% |
| M84 | D391E | 245.61% |
| M85 | Q32L + E171D | 117.28% |
| M86 | I389M | 116.47% |
| M87 | I389F + N394D | 251.31% |
| M88 | L404Q | 149.03% |
| M89 | I389F + L404Q | 157.31% |
| M90 | V164L + K456R | 74.62% |
| M91 | K96R | 10.78% |
| M92 | Q32L + R442H | 14.82% |
| M93 | R442L | 46.52% |
| M94 | V252I | 75.41% |
| M95 | E424K | 48.17% |

The obtained beneficial mutation uses an iterative—error-prone PCR—directed screening method, and use the site-directed mutation technology to continuously improve the activity of the mutant strain and the tolerance to the organic solvent.

Different mutant strains are used as original strains for the tolerance site verification:

The plasmids of the different mutant strains are extracted, and the mutant strains are constructed by the site-directed mutation technology. The obtained mutant strains are subjected to the verification of tolerance sites in 35% of the dimethyl sulfoxide, and results are shown in Table 5:

TABLE 5

| Original strain (amino acid difference compare to ArS-ωTA) | Mutation site | | | | | |
|---|---|---|---|---|---|---|
| | G411D | Y384F | S186G | D391E | E171D | L404Q |
| C60Y + F164V + R442Q | ++ | ++ | +++ | ++ | ++ | + |
| L3S + V5S + F164V + C60Y + I180V + L370A | ++ | ++ | +++ | +++ | +++ | + |
| L3S + V5S + C60Y + F164V + L370A | ++ | ++ | +++ | ++ | ++ | + |
| L3S + V5S + C60Y + F164V + Q420R + L370A | ++ | ++ | +++ | +++ | +++ | + |
| C60Y + F164V + L370A | ++ | ++ | +++ | ++ | ++ | + |
| L3S + V5S + F164V + C60Y + L370A + G452S | ++ | ++ | ++ | ++ | ++ | + |

+ means that the enzyme tolerance improvement degree in 35% of the dimethyl sulfoxide is 1%~100%,
++ means that the enzyme tolerance improvement degree in 35% of the dimethyl sulfoxide is 100%~300%,
+++ means that the enzyme tolerance improvement degree in 35% of the dimethyl sulfoxide is 400%~600%.

It may be seen that the mutation sites obtained by random mutation+directed screening have a significant effect on increasing the tolerance of the strain in the organic solvent (dimethyl sulfoxide).

Tolerance verification: a tolerance improvement degree of the mutation site obtained by the error-prone PCR in 40% of the dimethyl sulfoxide Tolerance verification results of a beneficial mutation site obtained using M76(L3S+V5S+C60Y+F164V+A178L+S187A+I180V+L370A) as the original strain in 45% of the dimethyl sulfoxide are shown in Table 6.

TABLE 6

| Strain | Amino acid difference (compare to M76) | Tolerance improvement degree |
|---|---|---|
| M76 | N/A | Null |
| M96 | G411D + E424K | 59.47% |
| M97 | Y384F + L404Q | 56.18% |
| M98 | E424K + G411D | 82.19% |
| M99 | G411D + S186G | 406.83% |
| M100 | S186G + Q420R | 757.07% |
| M101 | G411D + A187S | 1269.27% |
| M102 | G411D + V164L + I389F + E424Q + K96R | 1220.24% |
| M103 | V164L + I389F + L404Q | 891.46% |
| M104 | G411D + M423K + A187S | 1311.22% |
| M105 | G411D + S186G + I389F + L404Q | 1441.71% |
| M106 | G411D + S186G + Y384F + V164L | 1027.07% |
| M107 | G411D + S186G + Y384F + V164L + E171D | 1659.27% |
| M108 | G411D + S186G + Y384F + I389F + L404Q | 2086.59% |
| M109 | G411D + S186G + Y384F + V164L + V252I | 1060.00% |
| M110 | G411D + S186G + Y384F + V164L + I389F + V252I | 1978.78% |
| M111 | G411D + S186G + Y384F + V164L + E424Q | 2036.34% |
| M112 | G411D + S186G + Y384F + I389F + V164L | 1915.61% |
| M113 | G411D + S186G + Y384F + V164L + I389F + V252I + L404Q | 2085.85% |
| M114 | G411D + S186G + Y384F + V164L + I389F + V252I + E424Q | 2225.85% |
| M115 | G411D + S186G + Y384F + V164L + I389F + V252I + L404Q + E171D | 2281.71% |
| M116 | G411D + S186G + Y384F + V164L + I389F + V252I + E424Q + M423K | 2228.05% |
| M117 | G411D + S186G + Y384F + V164L + I389F + V252I + L404Q + E171D + D391E | 2147.32% |
| M118 | G411D + S186G + Y384F + E424Q + K7N | 1237.04% |
| M119 | G411D + S186G + Y384F + E171D | 395.41% |
| M120 | G411D + S186G + Y384F + D391E | 297.45% |
| M121 | G411D + S186G + Y384F | 273.21% |
| M122 | G411D + R442L + L178A + A187S | 137.54% |

Tolerance verification: a tolerance improvement degree of the mutation site obtained by the error-prone PCR in 70% of methyl tert-butyl ether.

Tolerance verification results of a beneficial mutation site obtained using M76 (L3S+V5S+C60Y+F164V+A178L+S187A+I180V+L370A) as the original strain in 70% of the methyl tert-butyl ether are shown in Table 7.

TABLE 7

| Strain | Amino acid difference (compare to M76) | Tolerance improvement degree |
|---|---|---|
| M76 | N/A | Null |
| M96 | G411D + E424K | 37.79% |
| M97 | Y384F + L404Q | 57.63% |
| M98 | E424K + G411D | 107.45% |
| M99 | G411D + S186G | 294.79% |

TABLE 7-continued

| Strain | Amino acid difference (compare to M76) | Tolerance improvement degree |
|---|---|---|
| M100 | S186G + Q420R | 353.59% |
| M101 | G411D + A187S | 373.16% |
| M102 | G411D + V164L + I389F + E424Q + K96R | 462.54% |
| M103 | V164L + I389F + L404Q | 314.26% |
| M104 | G411D + M423K + A178S | 543.56% |
| M105 | G411D + S186G + I389F + L404Q | 561.26% |
| M106 | G411D + S186G + Y384F + V164L | 455.26% |
| M107 | G411D + S186G + Y384F + V164L + E171D | 600.39% |
| M108 | G411D + S186G + Y384F + I389F + L404Q | 685.05% |
| M109 | G411D + S186G + Y384F + V164L + V252I | 486.73% |
| M110 | G411D + S186G + Y384F + V164L + I389F + V252I | 698.92% |
| M111 | G411D + S186G + Y384F + V164L + E424Q | 806.69% |
| M112 | G411D + S186G + Y384F + I389F + V164L | 820.06% |
| M113 | G411D + S186G + Y384F + V164L + I389F + V252I + L404Q | 835.50% |
| M114 | G411D + S186G + Y384F + V164L + I389F + V252I + E424Q | 843.56% |
| M115 | G411D + S186G + Y384F + V164L + I389F + V252I + L404Q + E171D | 850.34% |
| M116 | G411D + S186G + Y384F + V164L + I389F + V252I + E424Q + M423K | 840.12% |
| M117 | G411D + S186G + Y384F + V164L + I389F + V252I + L404Q + E171D + D391E | 811.60% |
| M118 | G411D + S186G + Y384F + E424Q + K7N | 457.64% |
| M119 | G411D + S186G + Y384F + E171D | 274.31% |
| M120 | G411D + S186G + Y384F + D391E | 324.87% |
| M121 | G411D + S186G + Y384F | 398.67% |
| M122 | G411D + R442L + L178A + A187S | 357.69% |

The tolerance of the modified mutant protein in the solvents dimethyl sulfoxide and methyl tertiary ether is greatly improved, and the activity of the mutant at high pH is also verified.

High pH tolerance verification: the obtained mutants are verified for the activity in 40% of the dimethyl sulfoxide and 70% of the methyl tert-butyl ether under a condition of pH=10.0, after 16 hours the mutant substrate is basically completely conversation, and results are shown in Table 8.

TABLE 8

| | | pH = 10' 40% DMSO, 0.5 wt enzyme | | pH = 10, 70% MTBE, 0.5 wt enzyme | |
|---|---|---|---|---|---|
| Strain | Site (amino acid difference compare to ArS-ωTA) | 5 h | 16 h | 5 h | 16 h |
| M76 | L3S + V5S + C60Y + F164V + A178L + S187A + I180V + L370A | ND | <0.1% | ND | <0.1% |
| M110 | L3S + V5S + C60Y + F164L + A178L + S187A + I180V + L370A + G411D + S186G + Y384F + I389F + V252I | 45.50% | 90.55% | 75.10% | 91.78% |
| M113 | L3S + V5S + C60Y + F164L + A178L + S187A + I180V +L370A + G411D + S186G + Y384F + I389F + V252I + L404Q | 95.12% | 96.94% | 91.56% | 94.66% |
| M114 | L3S + V5S + C60Y + F164L + I180V + L370A + G411D + A178L + S186G + S187A + Y384F + V252I + I389F + E424Q | 76.61% | 93.41% | 91.86% | 95.06% |
| M115 | L3S + V5S + C60Y + F164L + I180V + L370A + G411D + A178L + S186G + S187A + Y384F + E171D + I389F + V252I + L404Q | 94.29% | 95.80% | 93.33% | 96.24% |
| M116 | 3S + V5S + C60Y + F164L + I180V + L370A + G411D + A178L + S186G + S187A + Y384F + I389F + V252I + E424Q + M423K | 68.30% | 92.40% | 92.70% | 95.46% |
| M117 | L3S + V5S + C60Y + F164L + A178L + S187A + I180V +L370A + G411D + S186G + Y384F + I389F + V252I + L404Q + E171D + D391E | 73.04% | 95.15% | 84.75% | 95.13% |
| M123 | C60Y + F164L + I180V + L370A + G411D + A178L + S186G + S187A + Y384F + E171D + I389F + V252I + L404Q | 95.12% | 93.17% | 90.67% | 95.49% |
| M124 | C60Y + F164V + I180V + L370A + G411D + A178L + S186G + S187A + Y384F + E424Q | 89.64% | 94.87% | 89.17% | 95.46% |

The obtained mutants are broken by ultrasonication, supernatant enzyme solution and precipitated enzyme solution are obtained by centrifuging, and SDS-PAGE is performed to detect the expression condition of the protein. Generally, the soluble expressed protein exists in the supernatant in a dissolved state, and the abnormally folded protein exists in the form of an inclusion body, namely a precipitated protein. After SDS-PAGE detection, results are shown in FIG. 1 (Note: Lane 1: Marker, Lane 2: ArS-Ωta soluble protein, Lane 3: ArS-Ωta protein inclusion body, Lane 4: Marker, Lane 5: mutant M115 soluble protein, and Lane 6: mutant M115 protein inclusion body), and the soluble expression of the optimal mutant protein is 4 times greater than that of the original bacteria.

According to a typical implementation mode of the disclosure, a transaminase mutant is provided.

An amino acid sequence of the transaminase mutant is an amino acid sequence obtained by mutation occurred in an amino acid sequence shown in SEQ ID NO: 1 (SEQ ID NO: 1: MGLTVQKINW EQVKEWDRKYLMRTF-STQNEYQPVPIESTEGDYLITPGGTRLL-DFFNQLCCVNLGQKNQKVNAAI KEALD-RYGFVWDTYATDYKAKAAKIIIEDILGDEDWPGKVR-FVSTGSEAVETALNIARLYTNRPLW TREHDYHGWTGGAATVTRLRSFRSGLVGENS-ESFSAQIPGSSCSSAVLMAPSSNTFQDSNGNYL KDENGELLSVKYTRRMIENYGPEQVAAVITE-VSQGVGSTMPPYEYVPQIRKMTKELGVLWISDEVL TGFGRTGKWFGYQHYGVQPDIITMGKGLSSSSLPA-GAVVSKEIAAFMDKHRWESVSTYAGHPV AMAAVCANLEVMMEENLVEQAKNSGEYIRSK-LELLQEKHKSIGNFDGYGLLWIVDIVNAKTKTPYV KLDRNFRHGMNPNQIPTQIIMEKALEKGVLIG-GAMPNTMRIGASLNVSRGDIDKAMDALDYALDYL ESGEWQQS), and the mutation includes at least one of the following mutation sites: position 3, position 5, position 8, position 25, position 32, position 45, position 56, position 59, position 60, position 84, position 86, position 164, position 176, position 178, position 180, position 187, position 197, position 206, position 207, position 242, position 245, position 319, position 324, position 326, position 328, position 370, position 397, position 414, position 416, position 424, position 436, position 437 and position 442. Preferably, the mutation includes at least one of the following mutation sites: L3S, V5S, I8A, I8S, F25L, F25T, Q32N, I45W, L59V, F56M, C60F, C60Y, F84V, W86H, W86L, W86P, W86N, F164M, F164V, F176Y, F176S, A178L, I180V, S187A, T197P, L206M, K207T, V242A, T245A, T245V, R319C, R324A, R324G, E326M, V328A, V328G, L370A, L370D, L370K, T397A, P414G, Q416A, E424D, E424T, A436S, A436G, A436P, A436N, A436Y, A436Q, A436E, M437S, M437A, R442T, R442S, R442Q and R442V; or an amino acid sequence of the transaminase mutant has the mutation sites in the mutated amino acid sequence, and has more than 80% identity with the mutated amino acid sequence.

The above transaminase mutant of the disclosure is based on the transaminase shown in SEQ ID NO: 1, and is mutated through a site-directed mutation method, thereby the amino acid sequence thereof is changed, so changes in protein structure and function are achieved, the transaminase mutant has high solubility expression characteristics and high activity characteristics, a reaction rate may be improved by the application of this mutant, the enzyme stability is improved, the amount of the enzyme is reduced, and the difficulty of post-treatment is reduced, so it may be suitable for industrial production.

A term "identity" used herein has the meaning generally known in the field, and those skilled in the art are also familiar with rules and standards for measuring the identity between different sequences. The sequences defined by the disclosure with different degrees of the identity must also have the improved tolerance of the transaminase to the organic solvent. In the above implementation mode, preferably the amino acid sequence of the transaminase mutant has the above identity and has or encodes the amino acid sequence with the improved tolerance to the organic solvent. Those skilled in the art may obtain such mutant sequences under the teaching of the disclosed content of the present disclosure.

Preferably, the mutation includes at least one of the following mutation site combinations: C60Y+F164V, L3S+V5S, L3S+V5S+F164V, L3S+V5S+C60Y, L3S+V5S+C60Y+F164V, I180V+L370A and L3S+V5S+L59V; more preferably, the mutation includes at least one of the following mutation site combinations: F164V+C60Y、E424D+A436G、C60Y+F164V+A436P、C60Y+F164V+A436N、W86P+F164V、F25L+L59V、F25T+F164V、C60Y+F164V+A436Y、C60Y+F164V+A436Q、C60Y+F164V+A436E、F164V+M437A、I8A+V328A、I8S+F164V、C60Y+F164V+L370A、C60Y+F164V+L370D、C60Y+F164V+L370K、I45W+F164V、C60Y+F164V+F176Y、C60Y+F176S+F164V、L3S+V5S+C60Y+F164V+L370A、C60Y+F164V+R442S、C60Y+F164V+R442Q、L3S+V5S+S187A+L370A+E424D、C60Y+F164V+R442T、L3S+V5S+E424D+L370A、L3S+V5S+F164V+C60Y+I180V+L370A、L3S+V5S+C60Y+F164V+A178L+L370A、L3S+V5S+F164V+T197P+L370A、L3S+V5S+V328A+E424D、L3S+V5S+L59V+L206M+L370A、L3S+V5S+L370A+E424D、L3S+V5S+F164V+K207T+L370A、L3S+V5S+S244A+L370A、L3S+V5S+F164V+T245A+L370A、L3S+V5S+F164V+T245V+V328A、L3S+V5S+F164V+L370A+T397A、L3S+V5S+L59V+F164V+R319C+L370A+T397A、L3S+V5S+L59V+F164V+L370A、L3S+V5S+L59V+L370A+A436G+Q416A、L3+V5S+L59V+L370A+A436G+R442Q、L3S+V5S+L59V+V328A+L370A+R442Q、L3S+V5S+L59V+L370A+R442L、L3S+V5S+L59V+C60Y+F164V+L370A+R442V、L3S+V5S+C60Y+F164V+A178L+S187A+I180V+L370A、L3S+V5S+C60Y+F164V+I180V+S187A+L370A+R442L.

According to a typical implementation mode of the disclosure, the mutation further includes at least one of the following mutation sites or mutation site combinations: position 7, position 32, position 96, position 164, position 171, position 186, position 252, position 384, position 389, position 391, position 394, position 404, position 411, position 420, position 423, position 424, position 442, position 452 and position 456; preferably, the mutation also includes at least one of the following mutation sites: K7N, Q32L, K96R, V164L, E171D, S186G, V252I, Y384F, I389M, I389F, D391E, N394D, L404Q, L404Q, G411D, Q420R, Q420K, M423K, E424R, E424K, E424Q, R442H, R442L, G452S and K456R. The mutation is performed through the site-directed mutation method, thereby its amino acid sequence is changed, and changes in protein structure and function are achieved. Through the directed screening method, the transaminases with the above mutation sites are obtained. Therefore, these transaminase mutants have good organic solvent tolerance and high pH tolerance, and have high soluble expression characteristics and high activity characteristics, a reaction rate may be improved by use of these mutants, the enzyme stability is improved, the amount of the enzyme is reduced, and the difficulty of post-treatment is reduced, so it may be suitable for industrial production.

More preferably, the mutation includes at least one of the following mutation site combinations: G411D+S186G, G411D+S186G+Y384F, G411D+S186G+Y384F+V164L, G411D+S186G+Y384F+V164L+I389F and G411D+S186G+Y384F+V164L+I389F+V252I; further preferably, the mutation includes at least one of the following mutation site combinations: L3S+V5S+C60Y+F164V+A178L+S187A+I180V+L370A+Y384F+G452S, L3S+V5S+C60Y+F164V+A178L+S187A+I180V+L370A+S186G+Q420R, L3S+V5S+C60Y+F164V+A178L+S187A+I180V+L370A+M423K, L3S+V5S+C60Y+F164V+A178L+S187A+I180V+L370A+Q420K+E424R, L3S+V5S+C60Y+F164V+A178L+S187A+I180V+L370A+K7N+E424Q, L3S+V5S+C60Y+F164V+A178L+S187A+I180V+L370A+D391E, L3S+V5S+C60Y+F164V+A178L+S187A+I180V+L370A+Q32L+E171D, L3S+V5S+C60Y+F164V+A178L+S187A+I180V+L370A+I389M, L3S+V5S+C60Y+F164V+A178L+S187A+I180V+L370A+I389F+N394D, L3S+V5S+C60Y+F164V+A178L+S187A+I180V+L370A+L404Q, L3S+V5S+C60Y+F164V+A178L+S187A+I180V+L370A+I389F+L404Q, L3S+V5S+C60Y+F164V+A178L+S187A+I180V+L370A+V164L+K456R, L3S+V5S+C60Y+F164V+A178L+S187A+I180V+L370A+K96R, L3S+V5S+C60Y+F164V+A178L+S187A+I180V+L370A+Q32L+R442H, L3S+V5S+C60Y+F164V+A178L+S187A+I180V+L370A+R442L, L3S+V5S+C60Y+F164V+A178L+S187A+I180V+L370A+V252I, L3S+V5S+C60Y+F164V+A178L+S187A+I180V+L370A+E424K, L3S+V5S+C60Y+F164V+A178L+S187A+I180V+L370A, L3S+V5S+C60Y+F164V+Q420R+L370A, L3S+V5S+F164V+C60Y+L370A+G452S, L3S+V5S+C60Y+F164V+A178L+S187A+I180V+L370A+G411D+E424K, L3S+V5S+C60Y+F164V+A178L+S187A+I180V+L370A+Y384F+L404Q, L3S+V5S+C60Y+F164V+A178L+S187A+I180V+L370A+E424K+G411D, L3S+V5S+C60Y+F164V+A178L+S187A+I180V+L370A+G411D+S186G, L3S+V5S+C60Y+F164V+A178L+S187A+I180V+L370A+S186G+Q420R, L3S+V5S+C60Y+F164V+A178L+I180V+L370A+G411D, L3S+V5S+C60Y+F164V+A178L+S187A+I180V+L370A+G411D+V164L+I389F+E424Q+K96R, L3S+V5S+C60Y+F164V+A178L+S187A+I180V+L370A+V164L+I389F+L404Q, L3S+V5S+C60Y+F164V+A178L+I180V+L370A+

G411D+M423K, L3S+V5S+C60Y+F164V+A178L+S187A+I180V+L370A+G411D+S186G+I389F+L404Q, L3S+V5S+C60Y+F164L+A178L+S187A+I180V+L370A+G411D+S186G+Y384F, L3S+V5S+C60Y+F164V+A178L+S187A+I180V+L370A+G411D+S186G+Y384F+V164L+E171D, L3S+V5S+C60Y+F164V+A178L+S187A+I180V+L370A+G411D+S186G+Y384F+I389F+L404Q, L3S+V5S+C60Y+F164L+A178L+S187A+I180V+L370A+G411D+S186G+Y384F+V252I, L3S+V5S+C60Y+F164L+A178L+S187A+I180V+L370A+G411D+S186G+Y384F+I389F+V252I, L3S+V5S+C60Y+F164L+A178L+S187A+I180V+L370A+G411D+S186G+Y384F+E424Q, L3S+V5S+C60Y+F164L+A178L+S187A+I180V+L370A+G411D+S186G+Y384F+I389F, L3S+V5S+C60Y+F164L+A178L+S187A+I180V+L370A+G411D+S186G+Y384F+I389F+V252I+L404Q, L3S+V5S+C60Y+F164L+A178L+S187A+I180V+L370A+G411D+S186G+Y384F+I389F+V252I+E424Q, L3S+V5S+C60Y+F164L+A178L+S187A+I180V+L370A+G411D+S186G+Y384F+I389F+V252I+L404Q+E171D, L3S+V5S+C60Y+F164L+A178L+S187A+I180V+L370A+G411D+S186G+Y384F+I389F+V252I+E424Q+M423K, L3S+V5S+C60Y+F164L+A178L+S187A+I180V+L370A+G411D+S186G+Y384F+I389F+V252I+L404Q+E171D+D391E, L3S+V5S+C60Y+F164V+A178L+S187A+I180V+L370A+G411D+S186G+Y384F+E424Q+K7N, L3S+V5S+C60Y+F164V+A178L+S187A+I180V+L370A+G411D+S186G+Y384F+E171D, L3S+V5S+C60Y+F164V+A178L+S187A+I180V+L370A+G411D+S186G+Y384F+D391E, L3S+V5S+C60Y+F164V+A178L+S187A+I180V+L370A+G411D+S186G+Y384F, L3S+V5S+C60Y+F164V+I180V+L370A+G411D+R442L, C60Y+F164L+I180V+L370A+G411D+A178L+S186G+S187A+Y384F+E171D+I389F+V252I+L404Q, C60Y+F164V+I180V+L370A+G411D+A178L+S186G+S187A+Y384F+E424Q, L3S+V5S+C60Y+F164V+A178L+S187A+I180V+L370A+G411D, C60Y+F164V+R442Q+G411D, L3S+V5S+F164V+C60Y+I180V+L370A+G411D, L3S+V5S+C60Y+F164V+L370A+G411D, L3S+V5S+C60Y+F164V+Q420R+L370A+G411D, C60Y+F164V+L370A+G411D, L3S+V5S+F164V+C60Y+L370A+G452S+G411D+Y384F, C60Y+F164V+R442Q+Y384F, L3S+V5S+F164V+C60Y+I180V+L370A+Y384F, L3S+V5S+C60Y+F164V+L370A+Y384F, L3S+V5S+C60Y+F164V+Q420R+L370A+Y384F, C60Y+F164V+L370A+Y384F, L3S+V5S+F164V+C60Y+L370A+G452S+Y384F, C60Y+F164V+R442Q+S186G, L3S+V5S+F164V+C60Y+I180V+L370A+S186G, L3S+V5S+C60Y+F164V+L370A+S186G, L3S+V5S+C60Y+F164V+Q420R+L370A+S186G, C60Y+F164V+L370A+S186G, L3S+V5S+F164V+C60Y+L370A+G452S+S186G, C60Y+F164V+R442Q+D391E, L3S+V5S+F164V+C60Y+I180V+L370A+D391E, L3S+V5S+C60Y+F164V+L370A+D391E, L3S+V5S+C60Y+F164V+Q420R+L370A+D391E, C60Y+F164V+L370A+D391E, L3S+V5S+F164V+C60Y+L370A+G452S+D391E, C60Y+F164V+R442Q+E171D, L3S+V5S+F164V+C60Y+I180V+L370A+E171D, L3S+V5S+C60Y+F164V+L370A+E171D, L3S+V5S+C60Y+F164V+Q420R+L370A+E171D, C60Y+F164V+L370A+E171D, L3S+V5S+F164V+C60Y+L370A+G452S+E171D, C60Y+F164V+R442Q+L404Q, L3S+V5S+F164V+C60Y+I180V+L370A+L404Q, L3S+V5S+C60Y+F164V+L370A+L404Q, L3S+V5S+C60Y+F164V+Q420R+L370A+L404Q, C60Y+F164V+L370A+L404Q, and L3S+V5S+F164V+C60Y+L370A+G452S+L404Q. Through the directed screening method, the transaminases with the above mutation sites are obtained. Therefore, these transaminase mutants have good organic solvent tolerance and high pH tolerance, and have high soluble expression characteristics and high activity characteristics, a reaction rate may be improved by use of these mutants, the enzyme stability is improved, the amount of the enzyme is reduced, and the difficulty of post-treatment is reduced, so it may be suitable for industrial production.

According to a typical implementation mode of the disclosure, a DNA molecule is provided. The DNA molecule encodes the above transaminase mutant tolerant to an organic solvent. The above transaminase mutant encoded by the DNA molecule has good organic solvent tolerance and high pH tolerance, and has high soluble expression characteristics and high activity characteristics.

The above DNA molecule of the disclosure may also exist in the form of an "expression cassette". The "expression cassette" refers to a linear or circular nucleic acid molecule, includes DNA and RNA sequences that may direct the expression of a specific nucleotide sequence in an appropriate host cell. Generally speaking, it includes a promoter operatively linked with a target nucleotide, and it is optionally operatively linked with a termination signal and/or other regulatory elements. The expression cassette may also include a sequence required for proper translation of the nucleotide sequence.

A coding region usually encodes the target protein, but also encodes a target functional RNA in sense or antisense direction, such as an antisense RNA or an untranslated RNA. The expression cassette containing the target polynucleotide sequence may be chimeric, it means that at least one of its components is heterologous to at least one of the other components thereof. The expression cassette may also be naturally existent, but obtained by efficient recombination for heterologous expression.

According to a typical implementation mode of the disclosure, a recombinant plasmid is provided. The recombinant plasmid contains any one of the above DNA molecules. The DNA molecule in the above recombinant plasmid is inserted in an appropriate position of the recombinant plasmid, so that the above DNA molecule may be replicated, transcribed or expressed correctly and smoothly.

Although a qualifier used in the disclosure to define the above DNA molecule is "containing", it does not mean that other sequences that are not related to its function may be arbitrarily added to both ends of the DNA sequence. It is known by those skilled in the art that in order to meet requirements of a recombination operation, it is necessary to add appropriate digestion sites of a restriction endonuclease at both ends of the DNA sequence, or additionally add a start codon, a stop codon and the like. Therefore, if closed-type expression is used to limit, these situations may not be truly covered.

A term "plasmid" used in the disclosure includes any plasmids, cosmids, bacteriophages or agrobacterium binary nucleic acid molecules in double-stranded or single-stranded linear or circular form, preferably a recombinant expression plasmid, or a prokaryotic expression plasmid or a eukaryotic expression plasmid, but preferably the prokaryotic expression plasmid. In some implementation schemes, the recombinant plasmid is selected from pET-22a(+), pET-22b(+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19. More preferably, the above recombinant plasmid is pET-22b(+).

According to a typical implementation mode of the disclosure, a host cell is provided, and the host cell contains any one of the above recombinant plasmids. The host cell suitable for the disclosure includes but is not limited to a prokaryotic cell, yeast or a eukaryotic cell. Preferably, the prokaryotic cell is eubacteria, such as gram-negative bacteria or gram-positive bacteria. More preferably, the prokaryotic cell is an *Escherichia coli* BL21 cell or an *Escherichia coli* DH5α competent cell.

According to a typical implementation mode of the disclosure, a method for producing a chiral amine is provided. The method includes a step of performing a catalytic transamination reaction on a ketone compound and an amino donor by transaminase, and the transaminase is any one of the above transaminase mutants tolerant to an organic solvent. Because the above transaminase mutant of the disclosure has good organic solvent tolerance and high pH tolerance, and has high soluble expression characteristics and high activity characteristics, the reaction rate may be improved by using the chiral amine prepared by the transaminase mutant of the disclosure, the enzyme stability is improved, the amount of the enzyme is reduced, and the difficulty of post-treatment is reduced. Further, the ketone compound is

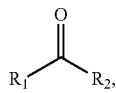

herein R1 and R2 each independently represent an optionally substituted or unsubstituted alkyl, an optionally substituted or unsubstituted aralkyl, or an optionally substituted or unsubstituted aryl; $R_1$ and $R_2$ may be singly or combined with each other to form a substituted or unsubstituted ring; preferably, $R_1$ and $R_2$ are optionally substituted or unsubstituted alkyl, optionally substituted or unsubstituted aralkyl, or optionally substituted or unsubstituted aryl having 1 to 20 carbon atoms, more preferably optionally substituted or unsubstituted alkyl, optionally substituted or unsubstituted aralkyl group, or optionally substituted or unsubstituted aryl having 1 to 10 carbon atoms;

preferably, the aryl includes phenyl, naphthyl, pyridyl, thienyl, oxadiazole group, imidazole group, thiazolyl, furanyl, pyrrolyl, phenoxy, naphthyloxy, pyridyloxy, thienyloxy, oxadiazoloxy, imidazoloxy, thiazolyloxy, furanyloxy and pyrrolyloxy;

preferably, the alkyl includes methyl, ethyl, propyl, butyl, pentyl, hexyl, isopropyl, sec-butyl, t-butyl, methoxy, ethoxy, t-butoxy, methoxy carbonyl, ethoxy carbonyl, t-butoxy carbonyl, vinyl, allyl, cyclopentyl and cycloheptyl;

preferably, the aralkyl is benzyl; and preferably, the substitution refers to substitution with halogen atom, nitrogen atom, sulfur atom, hydroxy, nitro, cyano, methoxy, ethoxy, carboxyl, carboxymethyl, carboxyethyl or methylenedioxy.

Preferably, the ketone compound is

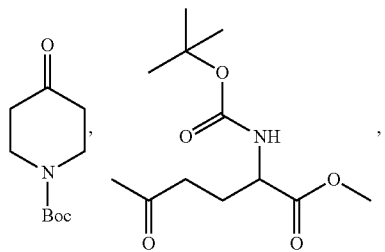

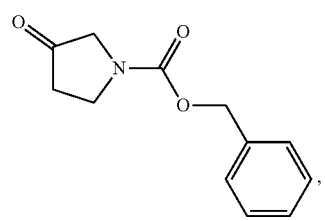

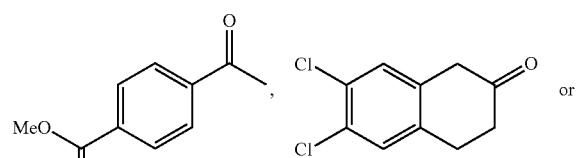 or

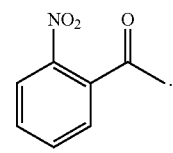

According to a typical implementation mode of the disclosure, the ketone compound is

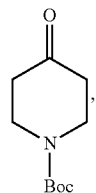

a transamination reaction product is

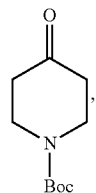

and a reaction formula is

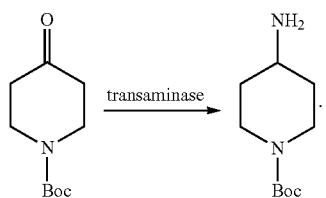 [SMILES: CC(C)(C)OC(=O)N1CCC(=O)CC1 ; CC(C)(C)OC(=O)N1CCC(N)CC1]

In a typical implementation mode of the disclosure, the amino donor is isopropylamine or alanine, preferably the isopropylamine.

In a reaction system the transaminase of the disclosure is applied to perform a catalytic transamination reaction on the ketone compound and the amino donor, a pH is 7-11, preferably 8-10, more preferably 9-10, in other words, the pH may be a value optionally selected from 7 to 11, such as 7, 7.5, 8, 8, 8.6, 9, 10, and 10.5. A temperature of the reaction system in which the transaminase is used to perform the catalytic transamination reaction on the ketone compound and the amino donor is 25-60° C., more preferably 30-55° C., further preferably 40-50° C., in other words, the temperature may be a value optionally selected from 25° C. to 60° C., such as 30, 31, 32, 35, 37, 38, 39, 40, 42, 45, 48, 50, 51, 52, and 55. The volume concentration of the dimethyl sulfoxide in the reaction system in which the transaminase is used to perform the catalytic transamination reaction on the ketone compound and the amino donor is 0%-50%, for example, 10%, 15%, 18%, 20%, 30%, 35%, 38%, 40%, 42%, 48%, and 49%. The volume concentration of the methyl tert-butyl ether in the reaction system in which the transaminase is used to perform the catalytic transamination reaction on the ketone compound and the amino donor is 0% to 90%, for example, 10%, 16%, 18%, 20%, 30%, 35%, 38%, 40%, 42%, 48%, 49%, 55%, 60%, 70%, 80%, and 90%.

It is known by those skilled in the art that many modifications may be made to the disclosure without departing from spirit of the disclosure, and such modifications also fall within a scope of the disclosure. In addition, the following experimental methods are conventional methods unless otherwise specified, and experimental materials used may be easily obtained from commercial companies unless otherwise specified.

Embodiment 1

Catalytic activity of ArS-ωTA mutant and wild enzyme on substrate 1 in organic solvent-free system:

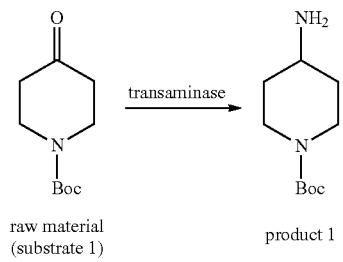 [SMILES: CC(C)(C)OC(=O)N1CCC(=O)CC1 ; CC(C)(C)OC(=O)N1CCC(N)CC1]

In a 10 mL reaction flask, 100 mg a raw material is added, 1 mg pyridoxal 5-phosphate is added, 2 mM isopropylamine hydrochloride is added, 250 μL crude enzyme solution of ArS-ωTA mutant or wild enzyme (0.05 g of mutant wet cells are ultrasonicated to prepare 20% of the crude enzyme solution, pH=8.5) is added, and 0.41 mL 100 mM PB8.5 is added, so that a final volume of the system is 1 mL, it is stirred at 30° C. for 16h, the system is centrifuged at 12000 rpm for 5 min, 200 μL sample is taken and 2 mL acetonitrile is added to dissolve. After being centrifuged at 12000 rpm for 5 min, the sample is sent for HPLC to detect a product conversion rate. Mutant information and results are shown in Table 9.

TABLE 9

| Strain | Sequence | Conversion rate (%) |
|---|---|---|
| ArS-ωTA | ArS-ωTA | <0.1% |
| M76 | L3S + V5S + C60Y + F164V + A178L + S187A + I180V + L370A | 95.93% |
| M110 | L3S + V5S + C60Y + F164L + A178L + S187A + I180V + L370A + G411D + S186G + Y384F + I389F + V252I | 98.01% |
| M113 | L3S + V5S + C60Y + F164L + A178L + S187A + I180V + L370A + G411D + S186G + Y384F + I389F + V252I + L404Q | 98.05% |
| M115 | L3S + V5S + C60Y + F164L + I180V + L370A + G411D + A178L + S186G + S187A + Y384F + E171D + I389F + V252I + L404Q | 98.61% |

It may be seen from the results in Table 9 that the catalytic activity of the ArS-ωTA mutant on the substrate 1 is greatly improved compared with the wild bacteria. After the modification of the disclosure, the catalytic activity of the ArS-ωTA mutant is greatly improved, the catalytic activity on an original non-catalyzed substrate is obtained, and a substrate spectrum is enlarged. At the same time, it may be seen that the conversion is carried out in a very small reaction volume, a utilization rate of a reactor is improved.

Embodiment 2

Catalytic activity of ArS-ωTA wild enzyme and mutant on substrate 1 in organic solvent system (40%) DMSO:

In a 10 mL reaction flask, 100 mg raw material (same as Embodiment 1) is added, 1 mg pyridoxal 5-phosphate is added, 2 mM isopropylamine hydrochloride is added, 250 μL crude enzyme solution of ArS-ωTA mutant or wild enzyme (0.05 g of mutant wet cells are ultrasonicated to prepare 20% of the crude enzyme solution, pH=8.5) is added, 0.01 mL 100 mM PB8.5 is added, and 0.4 mL dimethyl sulfoxide is added, so that a final volume of the system is 1 mL, it is stirred at 30° C. for 16h, the system is centrifuged at 12000 rpm for 5 min, 200 μL sample is taken and 2 mL acetonitrile is added to dissolve. After being centrifuged at 12000 rpm for 5 min, the sample is sent for HPLC to detect a product conversion rate. Mutant information and results are shown in Table 10.

TABLE 10

| Strain | Sequence | Conversion rate (%) |
|---|---|---|
| ArS-ωTA | ArS-ωTA | ND |
| M76 | L3S + V5S + C60Y + F164V + A178L + S187A + I180V + L370A | 4.75% |
| M110 | L3S + V5S + C60Y + F164L + A178L + S187A + I180V + L370A + G411D + S186G + Y384F + I389F + V252I | 80.51% |

TABLE 10-continued

| Strain | Sequence | Conversion rate (%) |
|---|---|---|
| M113 | L3S + V5S + C60Y + F164L + A178L + S187A + I180V + L370A + G411D + S186G + Y384F + I389F + V252I + L404Q | 97.46% |
| M115 | L3S + V5S + C60Y + F164L + I180V + L370A + G411D + A178L + S186G + S187A + Y384F + E171D + I389F + V252I + L404Q | 98.20% |

ND: No product generation detected

Embodiment 3

Chiral amine generated by catalyzing substrate through organic solvent-tolerant ArS-ωTA mutant and wild enzyme in 70% methyl tert-butyl ether solvent system:

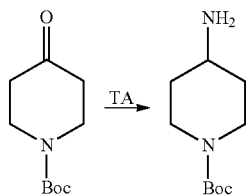

In a 10 mL reaction flask, 100 mg raw material (same as Embodiment 1) is added, 1 mg pyridoxal 5-phosphate is added, 2 mM isopropylamine hydrochloride is added, 250 μL crude enzyme solution of ArS-ωTA mutant or wild enzyme (0.05 g of mutant wet cells are ultrasonicated to prepare 20% of the crude enzyme solution, pH=8.5) is added, 1.4 mL methyl tert-butyl ether is added, so that a final volume of the system is 2 mL, it is stirred at 35° C. for 16h. After the system is centrifuged at 12000 rpm for 5 min, the methyl tert-butyl ether reagent is blown dry with nitrogen. 100 μL sample is taken from the remaining, and 2 ml acetonitrile is added to dissolve. After being centrifuged at 12000 rpm for 5 min, the sample is sent for HPLC to detect a product conversion rate, the conversion rate of the ArS-ωTA mutant is 95%, and the ArS-ωTA wild enzyme may not detect production of a product. Mutant information and results are shown in Table 11.

TABLE 11

| Strain | Sequence | Conversion rate (%) |
|---|---|---|
| ArS-ωTA | ArS-ωTA | 0% |
| M76 | L3S + V5S + C60Y + F164V + A178L + S187A + I180V + L370A | 12.01% |
| M110 | L3S + V5S + C60Y + F164L + A178L + S187A + I180V + L370A + G411D + S186G + Y384F + I389F + V252I | 95.58% |
| M113 | L3S + V5S + C60Y + F164L + A178L + S187A + I180V + L370A + G411D + S186G + Y384F + I389F + V252I + L404Q | 97.61% |
| M115 | L3S + V5S + C60Y + F164L + I180V + L370A + G411D + A178L + S186G + S187A + Y384F + E171D + I389F + V252I + L404Q | 97.57% |

Although the mutant M76 obtains the catalytic activity to the substrate 1 (Embodiment 3), in 40% of dimethyl sulfoxide, due to the low tolerance thereof to the organic solvent, most of the proteins are denatured to lose the activity, and the catalytic activity is greatly reduced. However, the mutants M113 and M115 still maintain the higher catalytic activity, it is indicated that the evolved mutant has greatly improved tolerance to the organic solvent dimethyl sulfoxide on the basis of acquiring the higher catalytic activity.

Embodiment 4

Catalytic activity verification of ArS-ωTA mutant and wild enzyme under different temperature and pH conditions

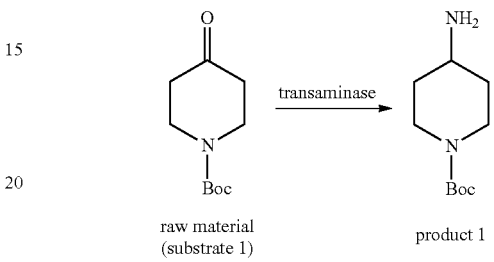

raw material (substrate 1)　　　　product 1

In a 10 mL reaction flask, 100 mg raw material is added, 1 mg pyridoxal 5-phosphate is added, 2 mM isopropylamine hydrochloride is added, and 500 μL crude enzyme solution of ArS-ωTA mutant M52 or M115 (0.1 g of mutant wet cells are ultrasonicated to prepare 20% of the crude enzyme solution, pH=11), or wild enzyme (1 g of mutant wet cells are ultrasonicated to prepare 20% of the crude enzyme solution, pH=11) is added, 100 mM phosphate buffer (pH=11) is added, so that a final volume of the system is 5.5 mL, it is stirred at 35° C. for 16h. After the system is centrifuged at 12000 rpm for 5 min, 200 μL sample is taken, and 2 mL acetonitrile is added to dissolve. After being centrifuged at 12000 rpm for 5 min, the sample is sent for HPLC to detect a product conversion rate.

Results show that even though the catalytic system of ArS-ωTA uses a lot of the enzyme (1 g wet cells) under an extreme pH condition, no product is detected after catalysis, and no product is detected in the catalytic system of mutant M52, while the catalytic system of mutant M115 uses the less enzyme (0.1 g), >80% of the product is detected, it is indicated that the mutant obtains the excellent high pH tolerance after modification, so that a catalytic space of the enzyme may be improved, and the double excellent characteristics of high activity and high pH tolerance make it suitable for the needs of the industrial production.

In a10 mL reaction flask, 100 mg raw material is added, 1 mg pyridoxal 5'-phosphate is added, 2 mM isopropylamine hydrochloride is added, and 500 μL crude enzyme solution of ArS-ωTA mutant M52 or M115 (0.1 g of mutant wet cells are ultrasonicated to prepare 20% of the crude enzyme solution, pH=8), or wild enzyme (1 g mutant wet cells are ultrasonicated to prepare 20% of the crude enzyme solution, pH=8) is added, 100 mM phosphate buffer (pH=8) is added, so that a final volume of the system is 5.5 mL, it is stirred at 60° C. for 16h. After the system is centrifuged at 12000 rpm for 5 min, 200 μL sample is taken, and 2 mL acetonitrile is added to dissolve. After being centrifuged at 12000 rpm for 5 min, the sample is sent for HPLC to detect a product conversion rate.

Results show that even though catalytic system of ArS-ωTA uses a lot of the enzyme (1 g wet cells) under an extreme pH condition, no product is detected after catalysis, and no product is detected in the catalytic system of mutant M52, while the catalytic system of mutant M115 uses the less enzyme (0.1 g), >80% of the product is detected, it is indicated that the mutant obtains the excellent high temperature tolerance after modification, so that a catalytic space of the enzyme may be improved, and the double excellent characteristics of high activity and high temperature tolerance make it suitable for the needs of the industrial production.

Embodiment 5

Chiral amine generated by catalyzing substrate through ArS-ωTA mutant and wild enzyme:

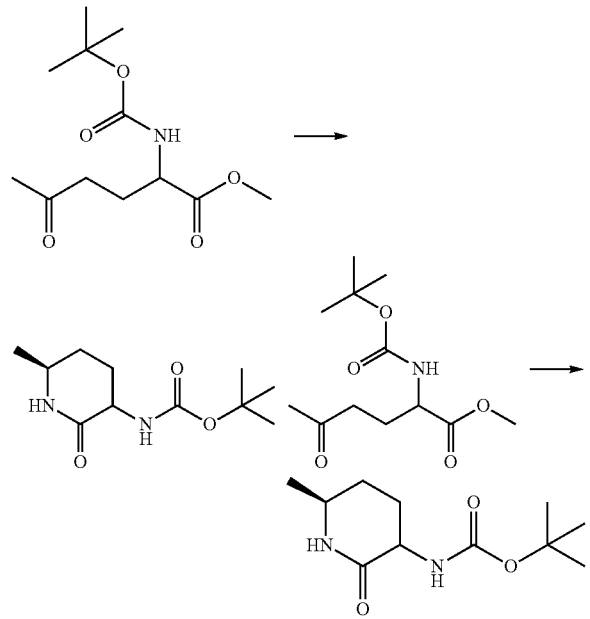

In a 10 mL reaction flask, 100 mg raw material is weighed, 1 mg pyridoxal 5'-phosphate is added, 2 mM isopropylamine hydrochloride is added, and 5 mL-250 μL crude enzyme solution of ArS-ωTA mutant (1 g-0.05 g-mutant wet cells are ultrasonicated to prepare 20% of the crude enzyme solution, pH=7.0 and pH=10.5), or wild enzyme (1 g-ArS-ωTA female parent wet cells are ultrasonicated to prepare 20% of the crude enzyme solution, pH=7.0 and pH=10.5) is added, 0.41 mL 100 mM phosphate buffer (pH=7.0) or phosphate buffer (pH=10.5) is added, so that a final volume of the system is 3 mL, it is stirred at 30° C. for 16h. After the system is centrifuged at 12000 rpm for 5 min, 200 NL sample is taken, and 2 mL acetonitrile is added to dissolve. After being centrifuged at 12000 rpm for 5 min, the sample is sent for HPLC to detect a product conversion rate.

Mutant information and results are shown in Table 12. The results show that the ArS-ωTA wild enzyme does not produce a product in the two pH systems of 7.0 and 10.5, while the product is detected in multiple mutants in the two pH systems, and some mutants show good activity, for example, the catalytic system of mutant M115 uses a very small amount of the enzyme (0.05 g, under a condition of pH=10.5), the conversion rate is >95%, and a chiral purity of the product is extremely high (>99%). The mutant obtained after modification of ArS-ωTA obtains the good catalytic activity, and at the same time, it may catalyze the production of the chiral amine at high pH, and the catalytic effect is good, it is indicated that the mutant achieves the qualitative breakthrough on catalytic activity and tolerance.

TABLE 12

| Number | Amino acid difference (compare to ArS-ωTA) | Activity |
| --- | --- | --- |
| ArS-ωTA | ArS-ωTA | ND |
| M29 | C60Y + F164V | + |
| M43 | C60Y + F164V + L370A | + |
| M26 | C60Y | ND |
| M14 | F164V | − |
| M52 | L3S + V5S + C60Y + F164V + L370A | +++ |
| M56 | C60Y + F164V + R442T | ++ |
| M6-2 | L3S + V5S + C60Y + F164V + L370A + Y384F + G452S | +++ |
| M104 | L3S + V5S + C60Y + F164V + I180V + L370A + G411D + A178L + M423K | ++ |
| M108 | L3S + V5S + C60Y + F164V + I180V + L370A + G411D + A178L + S186G + S187A + Y384F + I389F + L404Q | ++++ |
| M119 | L3S + V5S + C60Y + F164V + I180V + L370A + G411D + A178L + S186G + S187A + Y384F + E171D | ++++ |
| M120 | L3S + V5S + C60Y + F164V + I180V + L370A + G411D + A178L + S186G + S187A + Y384F + D391E | ++ |
| M101 | L3S + V5S + C60Y + F164V + I180V + L370A + G411D + A178L | +++ |
| M78 | L3S + V5S + C60Y + F164V + I180V + L370A + G411D + A178L + S187A | ++++ |
| M99 | L3S + V5S + C60Y + F164V + I180V + L370A + G411D + A178L + S186G + S187A | ++ |
| M121 | L3S + V5S + C60Y + F164V + I180V + L370A + G411D + A178L + S186G + S187A + Y384F | +++ |
| M106 | L3S + V5S + C60Y + F164V + I180V + L370A + G411D + A178L + S186G + S187A + Y384F + V164L | ++ |
| M109 | L3S + V5S + C60Y + F164V + I180V + L370A + G411D + A178L + S186G + S187A + Y384F + V164L + V252I | ++++ |
| M112 | L3S + V5S + C60Y + F164V + I180V + L370A + G411D + A178L + S186G + S187A + Y384F + V164L + I389F | ++ |
| M111 | L3S + V5S + C60Y + F164V + I180V + L370A + G411D + A178L + S186G + S187A + Y384F + V164L + E424Q | ++ |
| M110 | L3S + V5S + C60Y + F164V + I180V + L370A + G411D + A178L + S186G + S187A + Y384F + V164L + I389F + V252I | +++++ |
| M113 | L3S + V5S + C60Y + F164V + I180V + L370A + G411D + A178L + S186G + S187A + Y384F + V164L + I389F + V252I + L404Q | ++ |
| M114 | L3S + V5S + C60Y + F164V + I180V + L370A + G411D + A178L + S186G + S187A + Y384F + V164L + I389F + V252I++E424Q | ++ |
| M115 | L3S + V5S + C60Y + F164V + I180V + L370A + G411D + A178L + S186G + S187A + Y384F + V164L + I389F + V252I + L404Q + E171D | +++++ |
| M116 | L3S + V5S + C60Y + F164V + I180V + L370A + G411D + A178L + S186G + S187A + Y384F + V164L + I389F + V252I++E424Q + M423K | +++++ |
| M117 | L3S + V5S + C60Y + F164V + I180V + L370A + G411D + A178L + S186G + S187A + Y384F + V164L + I389F + V252I + L404Q + E171D + D391E | ++++ |

"ND" means that no product is detected by using 1 g wet cells for catalysis,
"−" means that <5% of the product is detected under a condition of pH = 7,
"+" means that 5%-20% of the product is detected under the condition of pH = 7,
"++" means that 20%-50% of the product is detected under the condition of pH = 7,
"+++" means that 50%-80% of the product is detected under the condition of pH = 7,
"++++" means that 80%-90% of the product is detected under the condition of pH = 7,
"+++++" means that 80%-95% of the product is detected under the condition of pH = 7, and at the same time, 90-100% of the product is detected by using 0.05 g wet cells for catalysis under a condition of pH = 10.5.

Embodiment 6

Chiral amine generated by catalyzing substrate through ArS-ωTA mutant and wild enzyme:

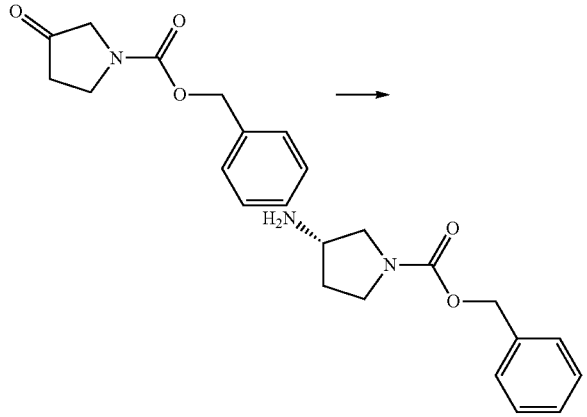

In a 10 mL reaction flask, 100 mg raw material is added, 1 mg pyridoxal 5-phosphate is added, 2 mM isopropylamine hydrochloride is added, and 100 μL crude enzyme solution of ArS-ωTA mutant (0.02 g mutant wet cells are ultrasonicated to prepare 20% of the crude enzyme solution, pH=8.5), or 1000 μL crude enzyme solution of wild enzyme (0.2 g ArS-ωTA wet cells are ultrasonicated to prepare 20% of the crude enzyme solution, pH=8.5) is added, 0.41 mL 100 mM PB8.5 is added, so that a final volume of the system is 3 mL, it is stirred at 30° C. for 16h. After the system is centrifuged at 12000 rpm for 5 min, 200 μL sample is taken, and 2 mL acetonitrile is added to dissolve. After being centrifuged at 12000 rpm for 5 min, the sample is sent for HPLC to detect a product conversion rate.

Mutant information and results are shown in Table 13. The results show that the catalytic system of ArS-ωTA wild enzyme uses 10 times of the amount of the enzyme of the mutant, but only a small amount of the product is produced (<20%). The catalytic system of mutants, such as M118 and M115, use very small amount of enzyme to obtain the conversion rates which are all >90%, and the chiral purity of the product is extremely high (>99%). At the same time, the activity of multiple mutants is greatly improved compared with that of the ArS-ωTA female parent, so the excellent catalytic effect is obtained.

TABLE 13

| Number | Amino acid difference (compare to ArS-ωTA) | Activity |
|---|---|---|
| ArS-ωTA | ArS-ωTA | − |
| M26 | C60Y | − |
| M14 | F164V | − |
| M43 | C60Y + F164V + L370A | + |
| M45 | C60Y + F164V + L370K | + |
| M48 | C60Y + F164V + F176S | + |
| M52 | L3S + V5S + C60Y + F164V + L370A | +++ |
| M54 | C60Y + F164V + R442Q | ++ |
| M36 | C60Y + F164V + A436Y | ++ |
| M3-2 | L3S + V5S + C60Y + F164V + L370A + Y384F | +++ |
| M3-6 | L3S + V5S + C60Y + F164V + L370A + L404Q | +++ |
| M6-2 | L3S + V5S + C60Y + F164V + L370A + Y384F + G452S | ++ |
| M3-1 | L3S + V5S + C60Y + F164V + L370A + G411D | +++ |
| M89 | L3S + V5S + C60Y + F164V + A178L + S187A + I180V + L370A + I389F + L404Q | +++ |

TABLE 13-continued

| Number | Amino acid difference (compare to ArS-ωTA) | Activity |
|---|---|---|
| M94 | L3S + V5S + C60Y + F164V + A178L + S187A + I180V + L370A + V252I | +++ |
| M88 | L3S + V5S + C60Y + F164V + A178L + S187A + I180V + L370A + I389F + L404Q | +++ |
| M4-3 | L3S + V5S + C60Y + F164V + L370A + S186G + Q420R | +++ |
| M104 | L3S + V5S + C60Y + F164V + I180V + L370A + G411D + A178L + M423K | +++ |
| M105 | L3S + V5S + C60Y + F164V + A178L + S187A + I180V + L370A + G411D + S186G + I389F + L404Q | +++ |
| M82 | L3S + V5S + C60Y + F164V + A178L + S187A + I180V + L370A + Q420K + E42R | ++++ |
| M92 | L3S + V5S + C60Y + F164V + A178L + S187A + I180V + L370A + Q32L + R442H | ++++ |
| M101 | L3S + V5S + C60Y + F164V + I180V + L370A + G411D + A178L | +++ |
| M122 | L3S + V5S + C60Y + F164V + I180V + L370A + G411D + R442L | +++ |
| M78 | L3S + V5S + C60Y + F164V + I180V + L370A + G411D + A178L + S187A | +++ |
| M109 | L3S + V5S + C60Y + F164L + I180V + L370A + G411D + A178L + S186G + S187A + Y384F + V252I | +++ |
| M112 | L3S + V5S + C60Y + F164L + I180V + L370A + G411D + A178L + S186G + S187A + Y384F + I389F | +++ |
| M111 | L3S + V5S + C60Y + F164L + I180V + L370A + G411D + A178L + S186G + S187A + Y384F + E424Q | +++ |
| M110 | L3S + V5S + C60Y + F164L + I180V + L370A + G411D + A178L + S186G + S187A + Y384F + I389F + V252I | ++++ |
| M108 | L3S + V5S + C60Y + F164L + I180V + L370A + G411D + A178L + S186G + S187A + Y384F + I389F + L404Q | ++++ |
| M118 | L3S + V5S + C60Y + F164L + I180V + L370A + G411D + A178L + S186G + S187A + Y384F + K7N + E424Q | ++++ |
| M119 | L3S + V5S + C60Y + F164L + I180V + L370A + G411D + A178L + S186G + S187A + Y384F + E171D | +++ |
| M120 | L3S + V5S + C60Y + F164L + I180V + L370A + G411D + A178L + S186G + S187A + Y384F + D391E | +++ |
| M113 | L3S + V5S + C60Y + F164L + I180V + L370A + G411D + A178L + S186G + S187A + Y384F + I389F + V252I + L404Q | ++++ |
| M114 | L3S + V5S + C60Y + F164L + I180V + L370A + G411D + A178L + S186G + S187A + Y384F + I389F + V252I ++ E424Q | ++++ |
| M115 | L3S + V5S + C60Y + F164L + I180V + L370A + G411D + A178L + S186G + S187A + Y384F + I389F + V252I + L404Q + E171D | ++++ |
| M116 | L3S + V5S + C60Y + F164L + I180V + L370A + G411D + A178L + S186G + S187A + Y384F + I389F + V252I ++ E424Q + M423K | ++++ |
| M117 | L3S + V5S + C60Y + F164L + I180V + L370A + G411D + A178L + S186G + S187A + Y384F + I389F + V252I + L404Q + E171D + D391E | ++++ |

"−" means that the conversion rate obtained by the original strain using 10 times of the amount of the enzyme (0.2 g) of the mutant is less than 20%, or the conversion rate obtained by the mutant using the same amount of the enzyme (0.2 g) as the original strain is reduced or not increased,
"+" means that the mutant uses a very small amount of the enzyme (0.02 g) to increase the conversion rate by 0.2-1 time,
"++" means that the mutant uses a very small amount of the enzyme (0.02 g) to increase the conversion rate by 1-2 times,
"+++" means that the mutant uses a very small amount of the enzyme (0.02 g) to increase the conversion rate by 2-4 times, and
"++++" means that the mutant uses a very small amount of the enzyme (0.02 g) to increase the conversion rate by more than 4 times.

Embodiment 7

Chiral amine generated by catalyzing substrate through ArS-ωTA mutant and wild enzyme:

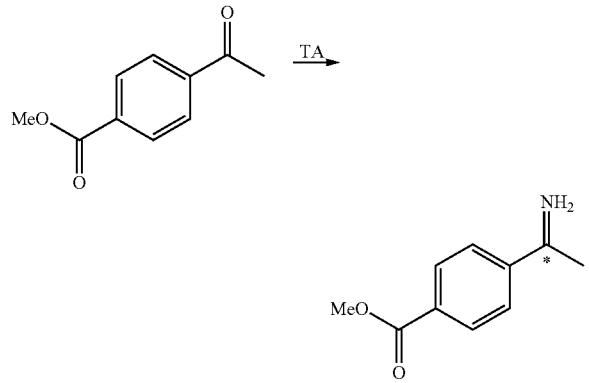

In a 10 mL reaction flask, 100 mg raw material is added, 1 mg pyridoxal 5-phosphate is added, 2 mM isopropylamine hydrochloride is added, 5 mL ArS-ωTA female parent and mutant crude enzyme solution (1 g mutant wet cells are ultrasonicated to prepare 20% of the crude enzyme solution, pH=8), 100 mM phosphate buffer (pH=8) is added, so that a final volume of the system is 5.5 mL, it is stirred at 35° C. for 16h. After the system is centrifuged at 12000 rpm for 5 min, 200 μL sample is taken, and 2 mL acetonitrile is added to dissolve. After being centrifuged at 12000 rpm for 5 min, the sample is sent for HPLC to detect a product conversion rate.

Mutant information and results are shown in Table 14. It may be seen that the activity of the transformed mutant is significantly improved compared with the original strain ArS-ωTA, and the chiral purity of the product is extremely high (>99%).

TABLE 14

| Number | Amino acid difference (compare to ArS-ωTA) | Activity |
| --- | --- | --- |
| ArS-ωTA | ArS-ωTA | + |
| M99 | L3S + V5S + C60Y + F164V + I180V + L370A + G411D + A178L + S186G + S187A | ++ |
| M6-2 | L3S + V5S + C60Y + F164V + L370A + Y384F + G452S | +++ |
| M56 | C60Y + F164V + R442T | +++ |
| M54 | C60Y + F164V + R442Q | +++ |
| M45 | C60Y + F164V + L370K | ++++ |
| M4-3 | L3S + V5S + C60Y + F164V + L370A ++ S186G + Q420R | +++ |
| M43 | C60Y + F164V + L370A | ++++ |
| M36 | C60Y + F164V + A436Y | +++ |
| M3-1 | L3S + V5S + C60Y + F164V + L370A + G411D | +++ |
| M2-1 | L3S + V5S + C60Y + F164V + L370A + I180V + G411D | +++ |
| M178 | L3S + V5S + C60Y + F164V + I180V + L370A + G411D + A178L + S187A | +++ |
| M122 | L3S + V5S + C60Y + F164V + I180V + L370A + G411D + R442L | ++ |
| M121 | L3S + V5S + C60Y + F164V + I180V + L370A + G411D + A178L + S186G + S187A + Y384F | +++ |
| M113 | L3S + V5S + C60Y + F164V + I180V + L370A + G411D + A178L + S186G + S187A + Y384F + V164L + I389F + V252I + L404Q | +++ |
| M109 | L3S + V5S + C60Y + F164V + I180V + L370A + G411D + A178L + S186G + S187A + Y384F + V164L + V252I | +++ |

TABLE 14-continued

| Number | Amino acid difference (compare to ArS-ωTA) | Activity |
| --- | --- | --- |
| M106 | L3S + V5S + C60Y + F164V + I180V + L370A + G411D + A178L + S186G + S187A + Y384F + V164L | +++ |
| M101 | L3S + V5S + C60Y + F164V + I180V + L370A + G411D + A178L | +++ |

"+" means that the conversion rate is less than 20%,
"++" means that the conversion rate is 20%-30%,
"+++" means that the conversion rate is 30%-40%, and
"+++" means that the conversion rate is 40%-50%

Embodiment 8

Chiral amine generated by catalyzing substrate through ArS-ωTA mutant and wild enzyme:

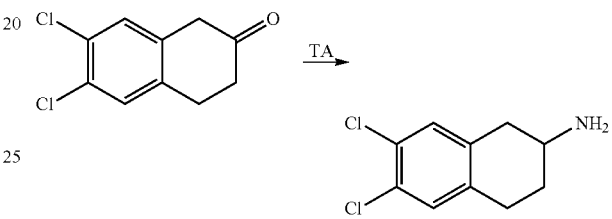

In a 10 mL reaction flask, 100 mg raw material is added, 1 mg pyridoxal 5-phosphate is added, 2 mM isopropylamine hydrochloride is added, 5 mL or 500 μL of crude enzyme solution (g ArS-Ωta or mutant wet cells are ultrasonicated to prepare 20% of the crude enzyme solution, pH=8), 100 mM phosphate buffer (pH=8) is added, so that a final volume of the system is 5.5 mL, it is stirred at 35° C. for 16h. After the system is centrifuged at 12000 rpm for 5 min, 200 μL sample is taken, a pH is adjusted to 10 with NaOH, and 2 mL MTBE is added to extract. After being centrifuged at 12000 rpm for 5 min, the sample is sent for HPLC to detect a product conversion rate.

Mutant information and results are shown in Table 15. It may be seen that the activity of the transformed mutant is significantly improved compared with the original strain ArS-ωTA. Multiple mutants may convert all the substrates into the product within 16 h, and the chiral purity of the product is extremely high (>99%).

TABLE 15

| Number | Amino acid difference (compare to ArS-ωTA) | Activity |
| --- | --- | --- |
| ArS-ωTA | ArS-ωTA | ++ |
| M29 | C60Y + F164V | +++ |
| M36 | C60Y + F164V + A436Y | ++++ |
| M43 | C60Y + F164V + L370A | +++ |
| M48 | C60Y + F164V + F176S | ++++ |
| M52 | L3S + V5S + C60Y + F164V + L370A | +++ |
| M54 | C60Y + F164V + R442Q | ++++ |
| M99 | L3S + V5S + C60Y + F164V + I180V + L370A + G411D + A178L + S186G + S187A | ++++ |
| M112 | L3S + V5S + C60Y + F164V + I180V + L370A + G411D + A178L + S186G + S187A + Y384F + V164L + I389F | ++++ |
| M113 | L3S + V5S + C60Y + F164V + I180V + L370A + G411D + A178L + S186G + S187A + Y384F + V164L + I389F + V252I + L404Q | ++++ |
| M114 | L3S + V5S + C60Y + F164V + I180V + L370A + G411D + A178L + S186G + S187A + Y384F + V164L + I389F + V252I + E424Q | ++++ |

TABLE 15-continued

| Number | Amino acid difference (compare to ArS-ωTA) | Activity |
|---|---|---|
| M115 | L3S + V5S + C60Y + F164V + I180V + L370A + G411D + A178L + S186G + S187A + Y384F + V164L + I389F + V252I + L404Q + E171D | ++++ |
| M119 | L3S + V5S + C60Y + F164V + I180V + L370A + G411D + A178L + S186G + S187A + Y384F + E171D | ++++ |
| M78 | L3S + V5S + C60Y + F164V + I180V + L370A + G411D + A178L + S187A | ++++ |

"++" means that the conversion rate obtained by using 1 g wet cells containing the target transaminase is less than 50%,
"+++" means that the conversion rate obtained by using 1 g wet cells containing the target transaminase is 70%-90%, and
"+++" means that the conversion rate obtained by using 0.1 g of wet cells containing the target transaminase is 90%-100%.

Embodiment 9

Chiral amine generated by catalyzing substrate through ArS-ωTA mutants (M52, M118 and M111) and wild enzyme:

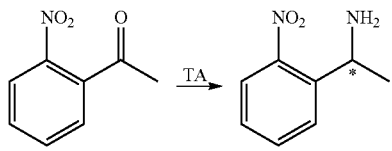

In a 10 mL reaction flask, 100 mg raw material is added, 1 mg pyridoxal 5-phosphate is added, 2 mM of isopropylamine hydrochloride is added, 5 mL crude enzyme solution (1 g ArS-Ωta or mutant wet cells are ultrasonicated to prepare 20% of the crude enzyme solution, pH=8), 100 mM phosphate buffer (pH=8) is added, so that a final volume of the system is 5.5 mL, it is stirred at 35° C. for 16h. After the system is centrifuged at 12000 rpm for 5 min, 200 µL sample is taken, and 2 mL acetonitrile is added to dissolve. After being centrifuged at 12000 rpm for 5 min, the sample is sent for HPLC to detect product. After being detected, it is found that the product may not be detected in the catalytic system of the starting bacteria ArS-Ωta, and the product is detected in all of the catalytic systems of M52, M118 and M111 mutants. It may be seen that the mutant obtains the catalytic activity to the substrate after the modification.

Embodiment 10

A single microbial colony of *Escherichia coli* containing each plasmid encoding the target transaminase is inoculated into 50 µg/Ml of an ampicillin-containing 50 mL Luria Bertani medium. Cells are cultured and grown overnight (about 16 h) in 37° C. shaker at 200 rpm. 5 mL culture is inoculated into a 2 L flask 50 mL Luria Bertani medium with 50 µg/Ml ampicillin, and cultured in 37° C. of the constant temperature shaker at 200 rpm until OD is 0.6 to 0.8, through adding isopropyl s D-sulfur Galactoside (IPTG) to a final concentration of 0.06 mM, the expression of a transaminase gene is induced, and then culture solution is continuously cultured in 25° C. of a constant temperature shaker at 200 rpm for about 16 h. The cells are collected by centrifugation (6000 rpm, 15 min, and 4° C.), and supernatant is discarded. The cells are resuspended in 100 mM phosphate buffer with a pH 7.0, the cells are lysed by ultrasonication to obtain a crude enzyme, and the crude enzyme is centrifuged (12000 rpm, 3 me, and 4° C.) to separate the supernatant and precipitate (including an inclusion body protein). The obtained precipitate is resuspended in an equal volume of 100 mM phosphate buffer with pH 7.0. An SOS-PAGE mode is used to detect expression conditions of soluble protein and inclusion body protein in the supernatant and precipitate.

Expression results of ArS-Ωta and each mutant are shown in Table 16, it is indicated that the introduction of mutation sites gradually makes the soluble expression condition of the mutant proteins better and better. The original bacteria ArS-ωTA only has a small amount of the protein expressed in the supernatant, and a large amount of the protein is expressed in the precipitate. The mutant M52 doubles the expression of the supernatant protein, but the final mutant M115 and the like make almost all the proteins expressed in the supernatant, and a very little protein is expressed in the precipitate. The expression condition of the mutant is greatly improved.

TABLE 16

| Number | Amino acid difference (compare to ArS-ωTA) | |
|---|---|---|
| ArS-ωTA | ArS-ωTA | − |
| M26 | C60Y | − |
| M14 | F164V | − |
| M29 | C60Y + F164V | − |
| M43 | C60Y + F164V + L370A | − |
| M52 | L3S + V5S + C60Y + F164V + L370A | + |
| M76 | L3S + V5S + C60Y + F164V + A178L + S187A + I180V + L370A | + |
| M121 | L3S + V5S + C60Y + F164V + I180V + L370A + G411D + A178L + S186G + S187A + Y384F | + |
| M108 | L3S + V5S + C60Y + F164V + I180V + L370A + G411D + A178L + S186G + S187A + Y384F + I389F + L404Q | ++ |
| M118 | L3S + V5S + C60Y + F164V + I180V + L370A + G411D + A178L + S186G + S187A + Y384F + K7N + E424Q | ++ |
| M109 | L3S + V5S + C60Y + F164V + I180V + L370A + G411D + A178L + S186G + S187A + Y384F + V164L + V252I | ++ |
| M112 | L3S + V5S + C60Y + F164V + I180V + L370A + G411D + A178L + S186G + S187A + Y384F + V164L + I389F | ++ |
| M110 | L3S + V5S + C60Y + F164V + I180V + L370A + G411D + A178L + S186G + S187A + Y384F + V164L + I389F + V252I | +++ |
| M113 | L3S + V5S + C60Y + F164V + I180V + L370A + G411D + A178L + S186G + S187A + Y384F + V164L + I389F + V252I + L404Q | ++++ |
| M114 | L3S + V5S + C60Y + F164V + I180V + L370A + G411D + A178L + S186G + S187A + Y384F + V164L + I389F + V252I + E424Q | ++++ |
| M115 | L3S + V5S + C60Y + F164V + I180V + L370A + G411D + A178L + S186G + S187A + Y384F + V164L + I389F + V252I + L404Q + E171D | ++++ |
| M116 | L3S + V5S + C60Y + F164V + I180V + L370A + G411D + A178L + S186G + S187A + Y384F + V164L + I389F + V252I + E424Q + M423K | +++ |
| M117 | L3S + V5S + C60Y + F164V + I180V + L370A + G411D + A178L + S186G + S187A + Y384F + V164L + I389F + V252I + L404Q + E171D + D391E | +++ |

"−" means a soluble expression level of the female parent ArS-ωTA: only a small amount is expressed in the supernatant, and the most is expressed in the precipitate;
"+" means that the soluble expression is increased by 1 time;
"++" means that the soluble expression is increased by 2 times;
"+++" means that the soluble expression is increased by more than 3 times; and
"++++" means that the soluble expression is increased by more than 4 times.

It may be seen from the above descriptions that the above embodiments of the disclosure achieve the following technical effects: the above transaminase mutant of the disclosure has good organic solvent tolerance and high pH tolerance, and has high soluble expression characteristics and high activity characteristics.

The above are only preferred embodiments of the disclosure, and are not used to limit the disclosure. Various modifications and changes may be made to the disclosure by those skilled in the art. Any modifications, equivalent replacements, improvements and the like made within the spirit and principle of the disclosure shall be included in the scope of protection of the disclosure.

What is claimed is:

1. A transaminase mutant having the sequence SEQ ID NO: 1 from Arthrobacter citreus with at least one of the following mutation site combinations:
C60Y+F164V, L3S+V5S, L3S+V5S+F164V, L3S+V5S+C60Y, L3+V5S+C60Y+F164V, I180V+L370A or L3S+V5S+L59V.

2. The transaminase mutant of claim 1, the transaminase mutant further comprises at least one of the following mutation site combinations: E424D+A436G, C60Y+F164V+A436P, C60Y+F164V+A436N, W86P+F164V, F25L+L59V, F25T+F164V, C60Y+F164V+A436Y, C60Y+F164V+A436Q, C60Y+F164V+A436E, F164V+M437A, I8A+V328A, I8S+F164V, C60Y+F164V+L370A, C60Y+F164V+L370D, C60Y+F164V+L370K, I45W+F164V, C60Y+F164V+F176Y, C60Y+F176S+F164V, L3S+V5S+C60Y+F164V+L370A, C60Y+F164V+R442S, C60Y+F164V+R442Q, L3S+V5S+S187A+L370A+E424D, C60Y+F164V+R442T, L3S+V5S+E424D+L370A, L3S+V5S+F164V+C60Y+I180V+L370A, L3S+V5S+C60Y+F164V+A178L+L370A, L3S+V5S+F164V+T197P+L370A, L3S+V5S+V328A+E424D, L3S+V5S+L59V+L206M+L370A, L3S+V5S+L370A+E424D, L3S+V5S+F164V+K207T+L370A, L3S+V5S+S244A+L370A, L3S+V5S+F164V+T245A+L370A, L3S+V5S+F164V+T245V+V328A, L3S+V5S+F164V+L370A+T397A, L3S+V5S+L59V+F164V+R319C+L370A+T397A, L3S+V5S+L59V+F164V+L370A, L3S+V5S+L59V+L370A+A436G+Q416A, L3S+V5S+L59V+L370A+A436G+R442Q, L3S+V5S+L59V+V328A+L370A+R442Q, L3S+V5S+L59V+L370A+R442L, L3S+V5S+L59V+C60Y+F164V+L370A+R442V, L3S+V5S+C60Y+F164V+A178L+S187A+I180V+L370A, and L3S+V5S+C60Y+F164V+I180V+S187A+L370A+R442L.

3. The transaminase mutant of claim 1, wherein the transaminase mutant further comprises at least one of the following mutation site combinations: G411D+S186G, G411D+S186G+Y384F, G411D+S186G+Y384F+V164L, G411D+S186G+Y384F+V164L+I389F and G411D+S186G+Y384F+V164L+I389F+V252I.

4. The transaminase mutant of claim 3, wherein the transaminase mutant comprises at least one of the following mutation site combinations:
L3S+V5S+C60Y+F164V+A178L+S187A+I180V+L370A+Y384F+G452S, L3S+V5S+C60Y+F164V+A178L+S187A+I180V+L370A+S186G+Q420R, L3S+V5S+C60Y+F164V+A178L+S187A+I180V+L370A+M423K, L3S+V5S+C60Y+F164V+A178L+S187A+I180V+L370A+Q420K+E424R, L3S+V5S+C60Y+F164V+A178L+S187A+I180V+L370A+K7N+E424Q, L3S+V5S+C60Y+F164V+A178L+S187A+I180V+L370A+D391E, L3S+V5S+C60Y+F164V+A178L+S187A+I180V+L370A+Q32L+E171D, L3S+V5S+C60Y+F164V+A178L+S187A+I180V+L370A+I389M, L3S+V5S+C60Y+F164V+A178L+S187A+I180V+L370A+I389F+N394D, L3S+V5S+C60Y+F164V+A178L+S187A+I180V+L370A+L404Q, L3S+V5S+C60Y+F164V+A178L+S187A+I180V+L370A+I389F+L404Q, L3S+V5S+C60Y+F164V+A178L+S187A+I180V+L370A+V164L+K456R, L3S+V5S+C60Y+F164V+A178L+S187A+I180V+L370A+K96R, L3S+V5S+C60Y+F164V+A178L+S187A+I180V+L370A+Q32L+R442H, L3S+V5S+C60Y+F164V+A178L+S187A+I180V+L370A+R442L, L3S+V5S+C60Y+F164V+A178L+S187A+I180V+L370A+V252I, L3S+V5S+C60Y+F164V+A178L+S187A+I180V+L370A+E424K, L3S+V5S+C60Y+F164V+A178L+S187A+I180V+L370A, L3S+V5S+C60Y+F164V+Q420R+L370A, L3S+V5S+F164V+C60Y+L370A+G452S, L3S+V5S+C60Y+F164V+A178L+S187A+I180V+L370A+G411D+E424K, L3S+V5S+C60Y+F164V+A178L+S187A+I180V+L370A+Y384F+L404Q, L3S+V5S+C60Y+

F164V+A178L+S187A+I180V+L370A+E424K+ G411D, L3S+V5S+C60Y+F164V+A178L+S187A+I180V+L370A+G411D+S186G, L3S+V5S+C60Y+F164V+A178L+S187A+I180V+L370A+S186G+Q420R, L3S+V5S+C60Y+F164V+A178L+I180V+L370A+G411D, L3S+V5S+C60Y+F164V+A178L+S187A+I180V+L370A+G411D+V164L+I389F+E424Q+K9 6R, L3S+V5S+C60Y+F164V+A178L+S187A+I180V+L370A+V164L+I389F+L404Q, L3S+V5S+C60Y+F164V+A178L+I180V+L370A+G411D+M423K, L3S+V5S+C60Y+F164V+A178L+S187A+I180V+L370A+G411D+S186G+I389F+L404Q, L3S+V5S+C60Y+F164L+A178L+S187A+I180V+L370A+G411D+S186G+Y384F, L3S+V5S+C60Y+F164V+A178L+S187A+I180V+L370A+G411D+S186G+Y384F+V164L+E1 71D, L3S+V5S+C60Y+F164V+A178L+S187A+I180V+L370A+G411D+S186G+Y384F+I389F+L40 4Q, L3S+V5S+C60Y+F164L+A178L+S187A+I180V+L370A+G411D+S186G+Y384F+V252I, L3S+V5S+C60Y+F164L+A178L+S187A+I180V+L370A+G411D+S186G+Y384F+I389F+V25 2I, L3S+V5S+C60Y+F164L+A178L+S187A+I180V+L370A+G411D+S186G+Y384F+E424Q, L3S+V5S+C60Y+F164L+A178L+S187A+I180V+L370A+G411D+S186G+Y384F+I389F, L3S+V5S+C60Y+F164L+A178L+S187A+I180V+L370A+G411D+S186G+Y384F+I389F+V25 2I+L404Q, L3S+V5S+C60Y+F164L+A178L+S187A+I180V+L370A+G411D+S186G+Y384F+I389F+V25 2I+E424Q, L3S+V5S+C60Y+F164L+A178L+S187A+I180V+L370A+G411D+S186G+Y384F+I389F+V25 2I+L404Q+E171D, L3S+V5S+C60Y+F164L+A178L+S187A+I180V+L370A+G411D+S186G+Y384F+I389F+V25 2I+E424Q+M423K, L3S+V5S+C60Y+F164L+A178L+S187A+I180V+L370A+G411D+S186G+Y384F+I389F+V25 2I+L404Q+E171D+D391E, L3S+V5S+C60Y+F164V+A178L+S187A+I180V+L370A+G411D+S186G+Y384F+E424Q+K7N, L3S+V5S+C60Y+F164V+A178L+S187A+I180V+L370A+G411D+S186G+Y384F+E171D, L3S+V5S+C60Y+F164V+A178L+S187A+I180V+L370A+G411D+S186G+Y384F+D391E, L3S+V5S+C60Y+F164V+A178L+S187A+I180V+L370A+G411D+S186G+Y384F, L3S+V5S+C60Y+F164V+I180V+L370A+G411D+R442L, C60Y+F164L+I180V+L370A+G411D+A178L+S186G+S187A+Y384F+E171D+I389F+V252I +L404Q, C60Y+F164V+I180V+L370A+G411D+A178L+S186G+S187A+Y384F+E424Q, L3S+V5S+C60Y+F164V+A178L+S187A+I180V+L370A+G411D, C60Y+F164V+R442Q+G411D, L3S+V5S+F164V+C60Y+I180V+L370A+G411D, L3S+V5S+C60Y+F164V+L370A+G411D, L3S+V5S+C60Y+F164V+Q420R+L370A+G411D, C60Y+F164V+L370A+G411D, L3S+V5S+F164V+C60Y+L370A+G452S+G411D+Y384F, C60Y+F164V+R442Q+Y384F, L3S+V5S+F164V+C60Y+I180V+L370A+Y384F, L3S+V5S+C60Y+F164V+L370A+Y384F, L3S+V5S+C60Y+F164V+Q420R+L370A+Y384F, C60Y+F164V+L370A+Y384F, L3S+V5S+F164V+C60Y+L370A+G452S+Y384F, C60Y+F164V+R442Q+S186G, L3S+V5S+F164V+C60Y+I180V+L370A+S186G, L3S+V5S+C60Y+F164V+L370A+S186G, L3S+V5S+C60Y+F164V+Q420R+L370A+S186G, C60Y+F164V+L370A+S186G, L3S+V5S+F164V+C60Y+L370A+G452S+S186G, C60Y+F164V+R442Q+D391E, L3S+V5S+F164V+C60Y+I180V+L370A+D391E, L3S+V5S+C60Y+F164V+L370A+D391E, L3S+V5S+C60Y+F164V+Q420R+L370A+D391E, C60Y+F164V+L370A+D391E, L3S+V5S+F164V+C60Y+L370A+G452S+D391E, C60Y+F164V+R442Q+E171D, L3S+V5S+F164V+C60Y+I180V+L370A+E171D, L3S+V5S+C60Y+F164V+L370A+E171D, L3S+V5S+C60Y+F164V+Q420R+L370A+E171D, C60Y+F164V+L370A+E171D, L3S+V5S+F164V+C60Y+L370A+G452S+E171D, C60Y+F164V+R442Q+L404Q, L3S+V5S+F164V+C60Y+I180V+L370A+L404Q, L3S+V5S+C60Y+F164V+L370A+L404Q, L3S+V5S+C60Y+F164V+Q420R+L370A+L404Q, C60Y+F164V+L370A+L404Q, and L3S+V5S+F164V+C60Y+L370A+G452S+L404Q.

5. A DNA molecule, wherein the DNA molecule encodes the transaminase mutant of claim 1.

6. A recombinant plasmid, wherein the recombinant plasmid comprises the DNA molecule of claim 5.

7. The recombinant plasmid of claim 6, wherein the recombinant plasmid is pET-22a(+), pET-22b(+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a(+), pET-25b(+), pET-26b(+), pET-27b(+), pET-28a(+), pET-29a(+), pET-30a(+), pET-31b(+), pET-32a(+), pET-35b(+), pET-38b(+), pET-39b(+), pET-40b(+), pET-41a(+), pET-41b(+), pET-42a(+), pET-43a(+), pET-43b(+), pET-44a(+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

8. A host cell, wherein the host cell comprises the recombinant plasmid of claim 6.

9. The host cell of claim 8, wherein the host cell comprises prokaryotic cell, yeast or eukaryotic cell; preferably the prokaryotic cell is *Escherichia coli* BL21-DE3 cell or *Escherichia coli* Rosetta-DE3 cell.

10. A method for producing a chiral amine, comprising a step of using a transaminase to catalyze a transamination reaction of a ketone compound and an amino donor, wherein the transaminase is the transaminase mutant of claim 1.

11. The method of claim 10, wherein the ketone compound is

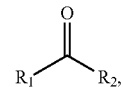

and the product of the transamination reaction is

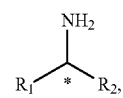

wherein $R_1$ and $R_2$ are each independently optionally substituted or unsubstituted alkyl, optionally substituted or unsubstituted aralkyl, or optionally substituted or unsubstituted aryl; and $R_1$ and $R_2$ can form a substituted or unsubstituted ring alone or in combination;

preferably, $R_1$ and $R_2$ are optionally substituted or unsubstituted alkyl, optionally substituted or unsubstituted aralkyl, or optionally substituted or unsubstituted aryl having 1 to 20 carbon atoms, more preferably optionally substituted or unsubstituted alkyl, optionally substituted or unsubstituted aralkyl group, or optionally substituted or unsubstituted aryl having 1 to 10 carbon atoms.

12. The method of claim 10, wherein the amino donor is isopropylamine or alanine, preferably isopropylamine.

13. The method of claim 10, wherein in a reaction system the transaminase catalyzes the transamination reaction of the ketone compound and the amino donor, the pH is 7 to 11, preferably 8 to 10, and more preferably 9 to 10.

14. The method of claim 11, wherein the aryl comprises phenyl, naphthyl, pyridyl, thienyl, oxadiazole group, imidazole group, thiazolyl, furanyl, pyrrolyl, phenoxy, naphthyloxy, pyridyloxy, thienyloxy, oxadiazoloxy, imidazoloxy, thiazolyloxy, furanyloxy and pyrrolyloxy.

15. The method of claim 12, wherein the alkyl comprises methyl, ethyl, propyl, butyl, pentyl, hexyl, isopropyl, sec-butyl, t-butyl, methoxy, ethoxy, t-butoxy, methoxy carbonyl, ethoxy carbonyl, t-butoxy carbonyl, vinyl, allyl, cyclopentyl and cycloheptyl;

preferably, the aralkyl is benzyl.

16. The method of claim 11, wherein the substitution refers to substitution with halogen atom, nitrogen atom, sulfur atom, hydroxy, nitro, cyano, methoxy, ethoxy, carboxyl, carboxymethyl, carboxyethyl or methylenedioxy, and preferably, the ketone compound is

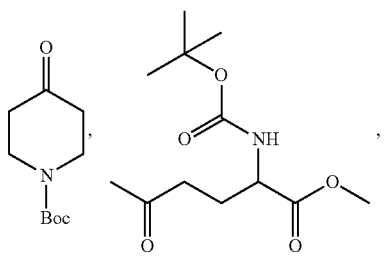

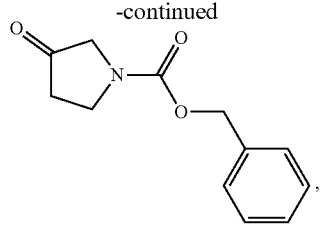

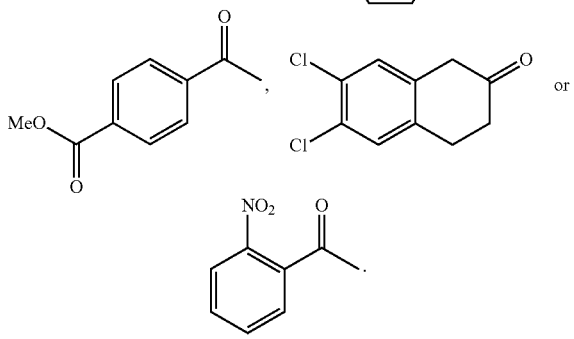

17. The method of claim 13, wherein in the reaction system the transaminase catalyzes the transamination reaction of the ketone compound and the amino donor, the temperature is 25° C. to 60° C., more preferably 30 to 55° C., and further preferably 40 to 50° C.

18. The method of claim 13, wherein a volume concentration of dimethyl sulfoxide in the reaction system the transaminase catalyzes the transamination reaction of the ketone compound and the amino donor is 0% to 50%.

19. The method of claim 18, wherein the volume concentration of methyl tert-butyl ether in the reaction system the transaminase catalyzes the transamination reaction of the ketone compound and the amino donor is 0% to 90%.

* * * * *

SEQUENCE LISTING

```
<160> NUMBER OF SEQ ID NOS: 1

<210> SEQ ID NO 1
<211> LENGTH: 476
<212> TYPE: PRT
<213> ORGANISM: Arthrobacter citreus

<400> SEQUENCE: 1

Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
                20                  25                  30

Pro Val Pro Ile Glu Ser Thr Glu Gly Asp Tyr Leu Ile Thr Pro Gly
            35                  40                  45

Gly Thr Arg Leu Leu Asp Phe Phe Asn Gln Leu Cys Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Cys Ser Ser Ala Val Leu Met Ala
            180                 185                 190

Pro Ser Ser Asn Thr Phe Gln Asp Ser Asn Gly Asn Tyr Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Val Pro Gln Ile Arg
                245                 250                 255

Lys Met Thr Lys Glu Leu Gly Val Leu Trp Ile Ser Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
```

```
305                 310                 315                 320
Asp Lys His Arg Trp Glu Ser Val Ser Thr Tyr Ala Gly His Pro Val
            325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
            355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
            405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
            435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475
```